(12) United States Patent
Balko et al.

(10) Patent No.: US 6,784,137 B2
(45) Date of Patent: Aug. 31, 2004

(54) 6-ARYL-4-AMINOPICOLINATES AND THEIR USE AS HERBICIDES

(75) Inventors: Terry William Balko, Greenfield, IN (US); Ann Marie Buysse, Carmel, IN (US); Jeffrey Brian Epp, Noblesville, IN (US); Stephen Craig Fields, Indianapolis, IN (US); Christian Thomas Lowe, Indianapolis, IN (US); Renee Joan Keese, Carmel, IN (US); John Sanders Richburg, III, Westfield, IN (US); James Melvin Ruiz, Zionsville, IN (US); Monte Ray Weimer, Pittsboro, IN (US); Renard Antonio Green, Indianapolis, IN (US); Roger Eugene Gast, Zionsville, IN (US); Kristy Bryan, Indianapolis, IN (US); Nicholas Martin Irvine, Westfield, IN (US); William Chi-Leung Lo, Fishers, IN (US); William Kirkland Brewster, Indianapolis, IN (US); Jeffery Dale Webster, New Palestine, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/209,448

(22) Filed: Jul. 30, 2002

(65) Prior Publication Data

US 2003/0114311 A1 Jun. 19, 2003

Related U.S. Application Data

(60) Provisional application No. 60/308,617, filed on Jul. 30, 2001.

(51) Int. Cl.$^7$ .................... A01N 43/40; C07D 213/04; C07D 401/00; C07D 421/00; C07D 419/00

(52) U.S. Cl. ................ 504/244; 504/251; 504/252; 504/254; 504/255; 504/260; 546/250; 546/268.4; 546/268.1; 546/255; 546/280.4; 546/281.7; 546/283.4

(58) Field of Search ................ 504/244, 251, 504/252, 254, 255, 260; 546/250, 268.1, 268.4, 280.4, 281.7, 283.4, 255

(56) References Cited

U.S. PATENT DOCUMENTS

| | | | |
|---|---|---|---|
| 3,234,229 A | 2/1966 | Redemann | 260/296 |
| 3,285,925 A | 11/1966 | Johnston et al. | 260/294.9 |
| 3,317,549 A | 5/1967 | Johnston | 260/294.9 |
| 3,325,272 A | 6/1967 | Hamaker et al. | 71/2.5 |
| 3,334,108 A | 8/1967 | Johnston | 260/294.8 |
| 3,755,338 A | 8/1973 | Gulbenk | 260/295 |
| 5,783,522 A | * 7/1998 | Schaefer et al. | 504/294 |
| 5,958,837 A | 9/1999 | Schaefer et al. | 504/244 |
| 6,077,650 A | 6/2000 | Price | 430/461 |
| 6,297,197 B1 | 10/2001 | Fields et al. | 504/260 |

FOREIGN PATENT DOCUMENTS

| | | |
|---|---|---|
| EP | 0972765 A1 | 6/1999 |
| WO | WO 98/21199 | 5/1998 |

\* cited by examiner

*Primary Examiner*—Alton N. Pryor
(74) *Attorney, Agent, or Firm*—Craig E. Mixan

(57) ABSTRACT

4-Aminopicolinic acids having aryl or heteroaryl substituents in the 6-position and their amine and acid derivatives are potent herbicides demonstrating a broad spectrum of weed control.

10 Claims, No Drawings

6-ARYL-4-AMINOPICOLINATES AND THEIR USE AS HERBICIDES

This application claims a priority from provisional application No. 60/308,617 which was filed on Jul. 30, 2001.

BACKGROUND OF THE INVENTION

This invention relates to certain novel 6-aryl-4-aminopicolinates and their derivatives and to the use of these compounds as herbicides.

A number of picolinic acids and their pesticidal properties have been described in the art. For example, U.S. Pat. No. 3,285,925 discloses 4-amino-3,5,6-trichloropicolinic acid derivatives and their use as plant growth control agents and herbicides. U.S. Pat. No. 3,325,272 discloses 4-amino-3,5-dichloropicolinic acid derivatives and their use for the control of plant growth. U.S. Pat. No. 3,317,549 discloses 3,6-dichloropicolinic acid derivatives and their use as plant growth control agents. U.S. Pat. No. 3,334,108 discloses chlorinated dithiopicolinic acid derivatives and their use as parasiticides. U.S. Pat. No. 3,234,229 discloses 4-amino-polychloro-2-trichloromethylpyridines and their use as herbicides. U.S. Pat. No. 3,755,338 discloses 4-amino-3,5-dichloro-6-bromopicolinates as fungicides. Belgian patent 788 756 discloses 6-alkyl-4-amino-3,5-dihalopicolinic acids as herbicides. In *Applied and Environmental Microbiology*, Vol. 59, No. 7, July 1993, pp. 2251–2256, 4-amino-3,6-dichloropicolinic acid is identified as a product of the anaerobic degradation of 4-amino-3,5,6-trichloropicolinic acid, the commercially available herbicide picloram. U.S. Pat. No. 6,297,197 B1 describes certain 4-aminopicolinates and their use as herbicides. U.S. Pat. No. 5,783,522 discloses certain 6-phenyl picolinic acids and their use as herbicides, desiccants and defoliating agents. WO 9821199 discloses 6-pyrazolylpyridines and their use as herbicides. U.S. Pat. No. 5,958,837 discloses the synthesis of 6-arylpicolinic acids and their use as herbicides, desiccants and defoliating agents. U.S. Pat. No. 6,077,650 discloses the use of 6-phenylpicolinic acids as photographic bleaching agents, and European Patent EP 0 972 765 A1 discloses the synthesis of 2-, 3- or 4-arylpyridines.

SUMMARY OF THE INVENTION

It has now been found that certain 6-aryl- or heteroaryl-4-aminopicolinic acids and their derivatives are potent herbicides with a broad spectrum of weed control against woody plants, grasses and sedges as well as broadleafs and with excellent crop selectivity. The compounds further possess excellent toxicological or environmental profiles.

The invention includes compounds of Formula I:

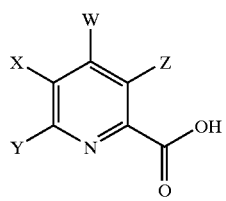

I wherein
X represents H, halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano;
Y represents aryl or heteroaryl;
Z represents halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano; and
W represents —$NO_2$, —$N_3$, —$NR_1R_2$, —$N{=}CR_3R_4$ or —$NHN{=}CR_3R_4$
wherein
$R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and
$R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with =C represent a 5- or 6-membered saturated ring; and
agriculturally acceptable derivatives of the carboxylic acid group.

Compounds of Formula I wherein X represents H or F wherein Y represents para-substituted phenyl with or without other substituents, wherein Z represents Cl, wherein W represents $NR_1R_2$ and $R_1$ and $R_2$ represent H or $C_1$–$C_6$ alkyl, are independently preferred. Also preferred are compounds wherein Y represents

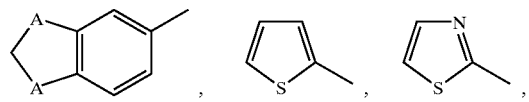

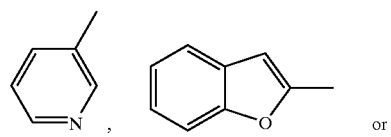  or

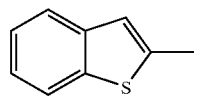

wherein A represents O or $CH_2$ and at least one of A is O. The aryl and heteroaryl groups which are represented by Y are preferably substituted with one or two groups independently selected from halogen, $C_1$–$C_2$ alkyl and $C_1$–$C_2$ haloalkyl.

The invention includes herbicidal compositions comprising a herbicidally effective amount of a compound of Formula I and agriculturally acceptable derivatives of the carboxylic acid group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 4-aminopicolinic acids of Formula II:

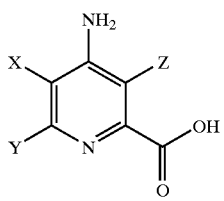

These compounds are characterized by possessing halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano substituents in the 3-position with halogen being preferred and chlorine being most preferred; by possessing hydrogen, halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano substituents in the 5-position with hydrogen and fluorine being preferred; and by possessing aryl and heteroaryl substituents in the 6-position with halogen, $C_1$–$C_2$ alkyl and $C_1$–$C_2$ haloalkyl substituted phenyl, pyridinyl, benzofuranyl, benzothienyl, thienyl and thiazoyl being preferred.

The amino group at the 4-position can be unsubstituted or substituted with one or more $C_1$–$C_6$ alkyl, $C_3$–$C_6$ alkenyl, $C_3$–$C_6$ alkynyl, aryl, heteroaryl, hydroxy, $C_1$–$C_6$ alkoxy or amino substituents. The amino group can be further derivatized as an amide, a carbamate, a urea, a sulfonamide, a silylamine, a phosphoramidate, an imine or a hydrazone. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the picolinic acid is derivatized to form a related substituent that can be transformed within plants or the environment to a acid group possess essentially the same herbicidal effect and are within the scope of the invention. Therefore, an "agriculturally acceptable derivative", when used to describe the carboxylic acid functionality at the 2-position, is defined as any salt, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 6-aryl or heteroaryl-4-aminopicolinic acid, and (b) is or can be hydrolyzed, oxidized or metabolized in plants or soil to the picolinic acid of Formula I that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 4-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 6-aryl or heteroaryl-4-aminopicolinic acid, and (b) is or can be hydrolyzed in plants or soil to a free amine of Formula II. N-Oxides which are also capable of breaking into the parent pyridine of Formula II are also covered by the scope of this invention.

Suitable salts include those derived from alkali or alkaline earth metals and those derived from ammonia and amines. Preferred cations include sodium, potassium, magnesium, and aminium cations of the formula:

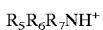

wherein $R_5$, $R_6$, and $R_7$ each, independently represents hydrogen or $C_1$–$C_{12}$ alkyl, $C_3$–$C_{12}$ alkenyl or $C_3$–$C_{12}$ alkynyl, each of which is optionally substituted by one or more hydroxy, $C_1$–$C_4$ alkoxy, $C_1$–$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$–$C_{12}$ alkyl, $C_3$–$C_{12}$ alkenyl or $C_3$–$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst. Suitable amides include those derived from ammonia or from $C_1$–$C_{12}$ alkyl, $C_3$–$C_{12}$ alkenyl or $C_3$–$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$–$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl", as well as derivative terms such as "aryloxy", refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The following heteroaryl groups are preferred:

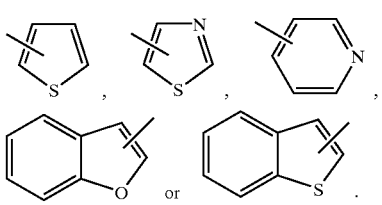

The aryl or heteroaryl substituents may be unsubstituted or substituted with one or more substituents selected from halogen, hydroxy, nitro, cyano, aryloxy, formyl, $C_1$–$C_6$ alkyl, $C_2$–$C_6$ alkenyl, $C_2$–$C_6$ alkynyl, $C_1$–$C_6$ alkoxy, halogenated $C_1$–$C_6$ alkyl, halogenated $C_1$–$C_6$ alkoxy, $C_1$–$C_6$ acyl, $C_1$–$C_6$ alkylthio, $C_1$–$C_6$ alkylsulfinyl, $C_1$–$C_6$ alkylsulfonyl, aryl, $C_1$–$C_6$OC(O)alklyl, $C_1$–$C_6$ NHC(O) alkyl, C(O)OH, $C_1$–$C_6$ C(O)alkyl, C(O)$NH_2$, $C_1$–$C_6$ C(O) NHalkyl, $C_1$–$C_6$ C(O)N(alkyl)$_2$, —OCH$_2$CH$_2$—, —OCH$_2$CH$_2$CH$_2$—, —OCH$_2$O— or —OCH$_2$CH$_2$O— provided that the substituents are sterically compatible and the rules of chemical bonding and strain energy are satisfied. Preferred substituents include halogen, $C_1$–$C_2$ alkyl and $C_1$–$C_2$ haloalkyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily synthesized utilizing standard procedures.

The 6-substituted aryl or heteroarylpyridines of Formula I can be prepared from a number of ways, which are well known in the art, e.g., by reaction of an appropriately substituted pyridine with a facile leaving group in the 6-position (III) with an organometallic compound of the type (IV) in an inert solvent in the presence of a transition metal catalyst.

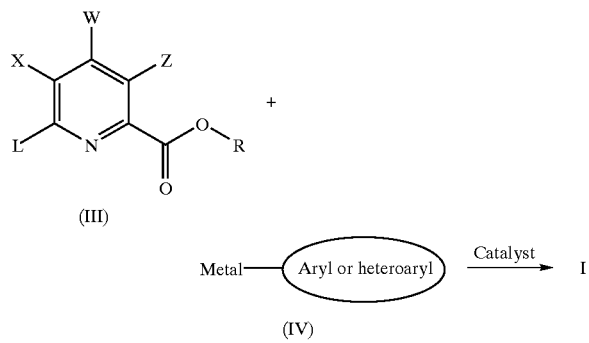

In this case "L" can be chlorine, bromine, iodo or trifluoromethanesulfonate, "Metal" can be Mg-halide, Zn-halide, tri-($C_1$–$C_4$ alkyl)tin, lithium, copper, or B(OR$^8$)(OR$^9$), where R$^8$ and R$^9$ are independently of one another, hydrogen, $C_1$–$C_4$ alkyl, or when taken together form an ethylene or propylene group, and "Catalyst" is a transition metal catalyst, in particular a palladium catalyst such as palladium diacetate, bis(triphenylphosphine)palladium(II) dichloride, or a nickel catalyst such as nickel(II) acetylacetonate, bis (triphenylphosphine)nickel(II) chloride.

Alternatively, compounds of Formula I can be prepared by reaction of an appropriately substituted 6-metal substituted pyridine (V) with an aryl or heteroaryl compound of the type (VI) in an inert solvent in the presence of a transition metal catalyst.

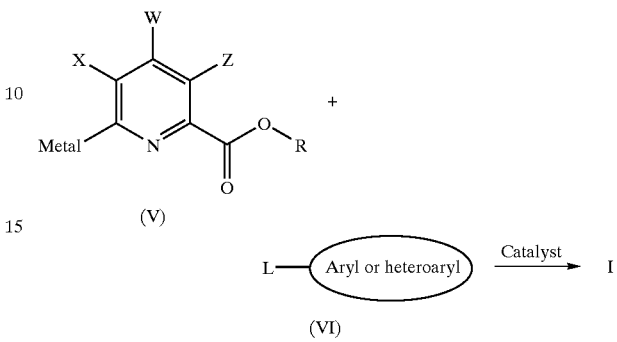

In this case "L" can be chlorine, bromine, iodo or trifluoromethanesulfonate and "Metal" can be Mg-halide, Zn-halide, tri-($C_1$–$C_4$ alkyl)tin, lithium, copper, or B(OR$^8$)(OR$^9$), where R$^8$ and R$^9$ are independently of one another, hydrogen, $C_1$–$C_4$ alkyl, or when taken together form an ethylene or propylene group, and "Catalyst" can be a transition metal catalyst, in particular a palladium catalyst such as palladium diacetate, bis(triphenylphosphine)palladium (II)dichloride, or a nickel catalyst such as nickel(II) acetylacetonate, bis (triphenylphosphine)nickel(II) chloride.

Reactions with boronic acids or esters are well known as exemplified by the following references:

(1) W. J. Thompson and J. Gaudino, J. Org. Chem., 49, 5223 (1984);
(2) S. Gronowitz and K. Lawitz, Chem. Scr., 24, 5 (1984);
(3) S. Gronowitz et al., Chem. Scr., 26, 305 (1986);
(4) J. Stavenuiter et al., Heterocycles, 26, 2711 (1987);
(5) V. Snieckus et al., Tetrahedron Letters, 28, 5093 (1987);
(6) V. Snieckus et al., Tetrahedron Letters, 29, 2135 (1988);
(7) M. B. Mitchell et al., Tetrahedron Letters, 32, 2273 (1991); Tetrahedron, 48, 8117 (1992);
(8) JP-A 93/301870.

Reactions with Grignard compounds (metal=Mg-Hal):
(9) L. N. Pridgen, J. Heterocyclic Chem., 12, 443 (1975);
(10) M. Kumada et al., Tetrahedron Letters, 21, 845 (1980);
(11) A. Minato et al., J. Chem. Soc. Chem. Commun., 5319 (1984).

Reaction with organozinc compounds (metal=Zn-Hal):
(12) A. S. Bell et al., Synthesis, 843 (1987);
(13) A. S. Bell et al., Tetrahedron Letters, 29, 5013 (1988);
(14) J. W. Tilley and S. Zawoiski, J. Org. Chem., 53, 386 (1988); see also ref (9).

Reactions with organotin compounds (metal=Sn($C_1$–$C_4$ (alkyl)$_3$):
(15) T. R. Bailey et al., Tetrahedron Letters, 27, 4407 (1986);
(16) Y. Yamamoto et al., Synthesis, 564 (1986); see also ref.(6)

The coupling of III+IV, or V+VI may, where appropriate, be followed by reactions on either ring to obtain further derivatives of the compounds of Formula I.

Alternativeley, compounds of Formula I can be prepared from compounds such as 3,4,5-trichloropicolinic acid. By using methods well known to one skilled in the art, the carboxylic acid can be converted into a heterocycle, i.e., the heteroaryl substituent.

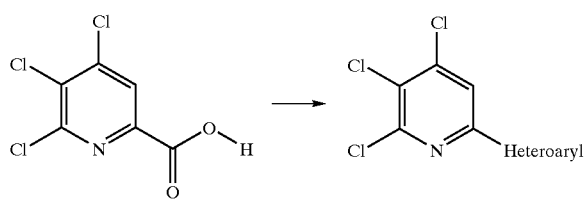

Appropriate reactions such as displacement of the corresponding 4-halopyridines with NaN$_3$, followed by reduction of the corresponding 4-azido derivatives provide an amino group at the 4-position. Carbonylation under standard conditions provides the carboxylic acid at the 2-position.

Appropriately substituted pyridines of Formula III where L is chloro, bromo, iodo or trifluoromethanesulfonate can be easily obtain by well-known methods; see WO 0151468. For example, 6-bromo analogs can be prepared by the reduction of several key intermediates, e.g., the corresponding 6-bromo-4-azido, 6-bromo-4-nitro, and 6-bromo-4-nitro pyridine N-oxide analogs. These intermediates, in turn, can be prepared either by nucleophilic displacement of 6-bromo-4-halo analogs with NaN$_3$ or by electrophilic nitration of the corresponding 6-bromopyridine-N-oxides. Alternatively, such analogs can be prepared by direct amination of the corresponding 4,6-dibromo analogs.

3- and 5-Alkoxy and aryloxy analogs can be prepared by reduction of the corresponding 4-azido derivatives, which in turn can be prepared by nucleophilic displacement of the corresponding 4-halopyridines with NaN$_3$. The required 3- and 5-alkoxy-4-halopyridines can be prepared according to literature procedures.

3- and 5-Alkylthio analogs can be prepared by lithiation of the appropriate chloropyridines at low temperature and sequential treatment with alkyl disulfides and carbon dioxide. Reaction of the resulting picolinic acids with ammonium hydroxide gives the desired products.

3- and 5-Cyano and thiocyanato analogs can be prepared by action of KCN and KSCN respectively on the appropriate fluoropyridine at high temperature. 3- and 5-Fluoro, bromo, iodo and nitro analogs can be prepared by electrophilic reaction of the unsubstituted precursor with positive halogen or nitro sources such as fluorine gas, bromine, iodine and fuming nitric acid, respectively.

3- and 5-Trifluoromethyl analogs can be prepared by standard manipulations known to those skilled in the art starting from the known compounds 2-fluoro-3-chloro-5-trifluoromethylpyridine and 2,5-dichloro-3-trifluoromethylpyridine.

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate. The imine or hydrazone can be prepared by reaction of the free amine or hydrazine with a suitable aldehyde or ketone.

Substituted 4-amino analogs can be prepared by reacting the corresponding 4-halopyridine-2-carboxylate or any other displaceable 4-substituent with the substituted amine.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds post-emergence. It is further usually preferred to use the compounds to control a wide spectrum of woody plants, broadleaf and grass weeds, and sedges. Use of the compounds to control undesirable vegetation in established crops is especially indicated. While each of the 6-aryl- or heteroaryl-4-aminopicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 2,000 g/Ha are generally employed in postemergence operations; for preemergence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, imazethapyr, imazapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, 4-amino-3,6-dichloropyridine-2-carboxylic acid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, propyzamide, simazine, norflurazon, paraquat, tebuthiuron, diuron, diflufenican, picolinafen, cinidon, sethoxydim, clethodim, tralkoxydim, quinmerac, isoxaben, bromoxynil and metribuzin. The herbicidal compounds of the present invention can, further, be used in conjunction with glyphosate and glufosinate on glyphosate-tolerant or glufosinate-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as cloquintocet, furilazole, dichlormid, benoxacor, mefenpyr-ethyl, fenclorazole-ethyl, flurazole, daimuron, dimepiperate, thiobencarb, fenclorim and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 6-aryl or heteroaryl-4-aminopicolinate compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims. Many of the starting materials useful for the preparation of the compounds of the present invention, e.g., 4-amino-3,6-dichloropyridine-2-carboxylic acid, 4-amino-3,5,6-trifluoro-2-cyanopyridine, methyl 4-amino-6-bromo-3,5-difluorpyridine-2-carboxylate and methyl 4-amino-6-bromo-3-chloropyridine-2-carboxylate, are described in U.S. Pat. No. 6,297,197 B1.

EXAMPLES

1. Preparation 5,6-Dichloropyridine-2-carboxylic Acid-N-oxide

50% Hydrogen peroxide (38 g, 0.35 mol) was carefully added to a mechanically stirred mixture of trifluoroacetic acid (350 mL) and 5,6-dichloropyridine-2-carboxylic acid (56.4 g, 0.29 mol) at 79° C. After one hour, the reaction mixture was poured into 1 L of saturated aqueous $NaHSO_3$, stirring vigorously and cooling in an ice bath. The precipitate was collected and dried to provide 5,6-dichloropyridine-2-carboxylic acid-N-oxide (62.9 g, 0.30 mol), mp 160° C.

2. Preparation of Methyl 5,6-Dichloropyridine-2-carboxylate-N-oxide

A suspension of 5,6-dichloropyridine-2-carboxylic acid-N-oxide (5.0 g, 24.0 mmol) in methanol (100 mL) was saturated with HCl gas and the reaction mixture heated at 40–50° C. for one hour. The solvent was removed and the residue dissolved in diethyl ether/ethyl acetate. The organic solution was washed with water, saturated sodium bicarbonate solution, brine, dried, and concentrated to give methyl 5,6-dichloropyridine-2-carboxylate-N-oxide (4.0 g, 18.1 mmol). $^1$H NMR (DMSO-$d_6$): δ 7.75 (s, 2H), 3.88 (s, 3H).

3. Preparation of Methyl 4.5.6-Trichloropyridine-2-carboxylate

A solution of methyl 5,6-dichloropyridine-2-carboxylate-N-oxide (22.0 g, 0.100 mol) and phosphorus oxychloride (15.70 mL, 0.169 mol) was heated at 70° C. for 36 hours. The solvent was removed and the residue carefully taken up into diethyl ether and water. The organic layer was washed with saturated sodium bicarbonate solution, water, brine, dried and concentrated to give methyl 4,5,6-trichloropyridine-2-carboxylate (20.0 g, 0.083 mol). $^1$H NMR (CDCl$_3$): δ 8.16 (s, 1H), 4.02 (s, 3H).

4. Preparation of 4,5,6-Trichloropyridine-2-carboxylic Acid

Methyl 4,5,6-trichloropyridine-2-carboxylate (10.11 g, 42 mmol) was suspended in dioxane (200 mL) and water (200 mL). To this mixture was added 1 N NaOH (42 mL, 42 mmol), and the reaction mixture was stirred at 25° C. After 72 h, 2 N NaOH (15 mL, 30 mmol) was added to drive the reaction to completion. The dioxane was removed by rotary evaporation, and the aqueous residue was acidified with concentrated hydrochloric acid. The precipitate was collected by suction filtration, washed with water and dried to provide 4,5,6-trichloropyridine-2-carboxylic acid (8.92 g, 39.6 mmol), mp 115–120° C.

5. Preparation of 4,5,6-Trichloropyridine-2-carbonyl Chloride

A solution of 4,5,6-trichloropyridine-2-carboxylic acid (5.20 g, 23.1 mmol) and thionyl chloride (3.0 mL) in dichloroethane (30 mL) was refluxed until the evolved gas ceased. The reaction mixture was concentrated to give 4,5,6-trichloropyridine-2-carbonyl chloride (5.60 g, 23.0 mmol), mp 60–62° C.

6. Preparation of (4,5,6-Trichloropyridin-2-yl)Methanol

Sodium borohydride (173 mg, 4.60 mmol) was added to a mixture of methyl 4,5,6-trichloropyridine-2-carboxylate (1.0 g, 4.16 mmol) in methanol (25 mL) at room temperature. After 40 min, the reaction was warmed to 50° C., and additional sodium borohydride (307 mg, 8 mmol) was added in 2 batches over the following 3 hours. The methanol was removed by rotary evaporation and the residue was diluted with 10% citric acid, aq. (50 mL) and stirred vigorously. The precipitate was collected, washed with water and dried to provide (4,5,6-trichloropyridin-2-yl)methanol (713 mg, 3.34 mmol), mp 82–83° C.

7. Preparation of 4,5,6-Trichloropyridine-2-carbaldehyde

A mixture of (4,5,6-trichloropyridin-2-yl)methanol (3.83 g, 18 mmol) and manganese (IV) oxide (7.8 g, 90 mmol) in dichloromethane (50 mL) was stirred at room temperature for 24 hours. More manganese (IV) oxide (4 g, 46 mmol) was added and stirring was continued. After another 24 hours, the reaction mixture was suction filtered through a silica gel plug (10 g). After washing the silica gel plug with additional dichloromethane (2×25 mL), manganese (IV) oxide (8 g, 92 mmol) was added to the filtrate, and the mixture was stirred at room temperature for 72 hours. The reaction mixture was refiltered and the solvent was removed to provide 4,5,6-trichloropyridine-2-carbaldehyde (2.36 g, 11.4 mmol), mp 84–88° C.

8. Preparation of 2,3,4-Trichloro-6-(5-oxazolyl)Pyridine

A mixture of 4,5,6-trichloropyridine-2-carbaldehyde (1.66 g, 8 mmol), tosylmethyl isocyanide (1.54 g, 8 mmol) and potassium carbonate (1.09 g, 8 mmol) in methanol (20 mL) was heated at 50° C. for 30 min and then heated at 80° C. for 5 min. The solvent was removed by rotary evaporation and the residue was suspended in water (200 mL) and stirred vigorously. The precipitate was collected by suction filtration, washed with water and air-dried to provide of 2,3,4-trichloro-6-(5-oxazolyl)pyridine (1.7 g, 6.8 mmol), mp 128–130° C.

9. Preparation of 4-azido-2,3-dichloro-6-(5-oxazolyl)Pyridine

A solution of 2,3,4-trichloro-6-(5-oxazolyl)pyridine (1.47 g, 5.9 mmol) and sodium azide (0.422 g, 6.5 mmol) in DMF (25 mL) was stirred at 50° C. under a nitrogen atmosphere for one hour. The reaction mixture was cooled and diluted with water (100 mL). The solid was filtered off and was dried to provide 4-azido-2,3-dichloro-6-(5-oxazoyl)pyridine (1.41 g, 5.5 mmol), mp 154–55° C.

10. Preparation of 4-amino-2,3-trichloro-6-(5-oxazolyl) pyridine

Sodium borohydride (0.174 g, 4.6 mmol) was added to a stirred suspension of 4-azido-2,3-dichloro-6-(5-oxazolyl) pyridine (1.17 g, 4.6 mmol) in methanol (25 mL) at room temperature. The solvent was removed and water (100 mL) was added to the residue. After 10 minutes of stirring, the solid formed was collected, washed with water and dried to give 4-amino-2,3-dichloro-6-(5-oxazolyl)pyridine (1.05 g, 4.55 mmol), mp 207–08° C.

The following compounds were prepared according to the procedure in Example 10:

4-Amino-5,6-dichloro-N-(2-hydroxyphenyl)pyridine-2-carboxamide: mp 248° C.

Methyl 4-amino-3-chloro-6-(5-bromo-2-thiazolyl)pyridine-2-carboxylate, (Compound 1): $^1$H NMR (CDCl$_3$): δ 7.90 (s, 1H), 7.67 (s, 1H), 6.52 (br.s, 2H), 3.97 (s, 3H).

Methyl 4-amino-3,5-dichloro-6-(5-chloro-2-furanyl) pyridine-2-carboxylate (Compound 2): $^1$H NMR (CDCl$_3$): δ 7.27 (d, J=5.5 Hz, 1H), 6.35 (d, J=5.5 Hz, 1H), 5.39 (br.s, 2H), 4.01 (s, 3H).

Methyl 4-amino-3-chloro-6-(1-methyl-1H-pyrazol-3-yl)pyridine-2-carboxylate (Compound 3): $^1$H NMR (CDCl$_3$): δ 7.39 (d, J=2.3 Hz, 1H), 7.38 (s, 1H), 6.86 (d, J=2.3 Hz, 1H), 4.90 (br.s, 2H), 4.01 (s, 3H), 3.97 (s, 3H).

Methyl 4-amino-3-chloro-6-(1-methyl-1H-pyrazol-5-yl)pyridine-2-carboxylate (Compound 4): $^1$H NMR (CDCl$_3$): δ 7.46 (d, J=2.1 Hz, 1H), 6.96 (s, 1H), 6.49 (d, J=2.1 Hz, 1H), 4.90 (br.s, 2H), 4.17 (s, 3H), 3.99 (s, 3H).

Methyl 4-amino-3-chloro-6-(3-pyrazolyl)pyridine-2-carboxylate (Compound 5): $^1$H NMR (CDCl$_3$): δ 7.62 (br.s, 11H), 7.24 (s, 1H), 6.75 (br.s, 1H), 4.98 (br.s, 2H), 4.01 (s, 3H).

Methyl 4-amino-3-chloro-6-(4-triazolyl)pyridine-2-carboxylate (Compound 6): $^1$H NMR (CDCl$_3$): δ 11.90 (br.s, 1H), 8.27 (s, 1H), 7.45 (s, 1H), 4.90 (br.s, 2H), 4.04 (s, 3H).

11. Preparation of Methyl 4-amino-3-chloro-6-(5-oxazolyl) Pyridine-2-carboxylate (Compound 7)

A solution of 4-amino-2,3-dichloro-6-(5-oxazolyl)pyridine (800 mg, 3.48 mmol), sodium acetate (571 mg, 6.96 mmol), palladium acetate (16 mg, 0.07 mmol), and 1,4-bis(diphenylphosphino)butane (30 mg, 0.07 mmol) in methanol (25 mL) was pressurized with carbon monoxide at 100 psi. After 12 hours at 100° C., the reaction mixture was cooled and concentrated. The residue was taken up into ethyl acetate and washed twice with water. The organic layer was dried (MgSO$_4$) and concentrated to provide methyl 4-amino-3-chloro-6-(5-oxazolyl)pyridine-2-carboxylate (788 mg, 3.10 mmol), mp 166–70° C.

The following compounds were prepared according to the procedure in Example 11:

Methyl 4-amino-3-chloro-6-(2-(5-methyl-1,3,4-thiadiazolyl))pyridine-2-carboxylate (Compound 8): mp 237–238° C.

Methyl 4-amino-3-chloro-6-(2-benzthiazolyl)pyridine-2-carboxylate (Compound 9): mp 224° C.

Methyl 4-amino-3-chloro-6-(1-methyl-1H-tetrazol-5-yl)pyridine-2-carboxylate (Compound 10): mp 239–241° C.

Methyl 4-amino-3-chloro-6-(2-methyl-2H-tetrazol-5-yl)pyridine-2-carboxylate (Compound 11): mp 250–252° C.

12. Preparation of 4,5,6-Trichloropyridine-2-dimethyliminochloride

N,N-Dimethyl 4,5,6-trichloropyridine-2-carboxamide (2.5 g, 0.01 mol) and dimethylformide (3 drops) in oxalyl chloride (10 mL) were heated to reflux for one hour. The reaction mixture was concentrated and the residual oil triturated with diethyl ether to give a pale yellow-brown hygroscopic solid which was used without further purification.

13. Preparation of 4,5,6-Trichloro-6-(2-benzthiazolyl) Pyridine

A solution of 2-aminobenzenethiol (1.40 mL, 0.013 mol) in dichloromethane was added dropwise to an ice-cooled mixture of 4,5,6-trichloro)pyridine-2-dimethyliminochloride (3.2 g, 0.013 mol), and triethylamine (2.0 mL) in dichloromethane (100 mL). After the addition, the reaction mixture was allowed to warm to room temperature over 2 hours. The solvent was then removed in vacuo and the crude product purified by column chormatography (0.5–1% diethyl ether in hexanes) to give 2,3,4-trichloro-6-(2-benzthiazolyl)pyridine (1.58 g, 0.005 mol). $^1$H NMR δ 8.44 (s, 1H) 8.10 (d, J=7.7 Hz, 1H), 7.98 (d,J=7.3 Hz, 1H), 7.51 (m, 2H).

14. Prepartion of 4,5,6-Trichloropyridine-2-carboxamide

Methyl 4,5,6-trichloropyridine-2-carboxylate (15 g, 62.4 mmol) was suspended in concentrated aqueous ammonium hydroxide (80 mL) and methanol (150 mL). After stirring for 4 hours at 25° C., the methanol was removed and the aqueous suspension was filtered. The filter cake was washed with water and dried to provide 4,5,6-trichloropyridine-2-carboxamide (13 g, 56.9 mmol), mp 169–170° C.

15. Preparation of 4,5,6-Trichlorolpyridine-2-carbonitrile 4,5,6-Trichloropyridine-2-carboxamide (8.0 g, 35.0 mmol) was suspended in acetonitrile (150 mL). To this mixture was added phosphorous oxychloride (6.6 mL, 70.0 mmol) and the reaction mixture was heated to reflux. After 16 hours, the volatiles were removed, and the residue was partitioned between saturated aqueous NaHCO$_3$ (200 mL) and ethyl acetate (200 mL). The organic layer was washed with brine (100 mL), dried (Na$_2$SO$_4$), and filtered through silica gel (10 g). The filtrate was evaporated to dryness to 4,5,6-trichloropyridine-2-carbonitrile (6.9 g, 33.3 mmol), mp 87–88° C.

16. Preparation of 2,3,4-Trichloro-6-(1H-tetrazol-5-yl) Pyridine

A mixture of 4,5,6-trichloropyridine-2-carbonitrile (4.77 g, 23.0 mmol), azidotrimethylsilane (6.1 mL, 46.0 mmol) and dibutyltin oxide (0.57 g, 2.3 mmol) in toluene (75 mL) was heated to 90° C. After 3 hours, the reaction mixture was heated to reflux. After 7 hours, azidotrimethylsilane (0.5 mL, 3.8 mmol) and dibutyltin oxide (100 mg, 0.4 mmol) were added to drive the reaction to completion. After a short time, the volatiles were removed, and then the residue was taken up in methanol (50 mL) and stirred briefly at 25° C. The volatiles were removed and the residue was partitioned between saturated aq. NaHCO$_3$ (200 mL), ethyl acetate (200 mL) and diethyl ether (100 mL). The layers were carefully separated in order to retain the insoluble white material in the aqueous fraction. The aqueous fraction then was acidified to pH 2 with concentrated HCl while stirring vigorously. The white precipitate was collected, washed with water and dried to provide 2,3,4-trichloro-6-(1H-tetrazol-5-yl)pyridine (5.4 g, 21.6 mmol), mp 197–198° C.

17. Preparation of 2,3,4-Trichloro-6-(1-methyl-1H-tetrazol-5-yl)Pyridine and 2,3,4-Trichloro-6-(2-methyl-1H-tetrazol-5-yl)pyridine A mixture of 2,3,4-trichloro-6-(1H-tetrazol-5-yl)pyridine (3.25 g, 13 mmol), iodomethane (1.84 g, 13 mmol), and potassium carbonate (1.79 g, 13 mmol) in dimethylformamide (100 mL) was stirred at 25° C. for 22 hours. The volatiles were removed and the residue purified by column chromatography (15% ethyl acetate in hexane) to provide 2,3,4-trichloro-6-(1-methyl-1H-tetrazol-5-yl)pyridine (1.66 g, 6.3 mmol), mp 138–141° C. and 2,3,4-trichloro-6-(2-methyl-1H-tetrazol-5-yl)pyridine (1.05 g, 4.0 mmol), mp 156–157° C.

18. Preparation of 4,5,6-Trichloro-(N'-2-acetyl)pyridine-2-carbohydrazide

A mixture of 4,5,6-trichloropyridine-2-carbonyl chloride (9.0 g, 37 mmol) in pyridine (100 mL) was cooled to 0° C., and acetic hydrazide (3.0 g, 40 mmol) was added. The ice bath was removed and after 2.5 h at 25° C., methanol (50 mL) was added and the reaction mixture was stirred briefly. The volatiles were removed and the residue was suspended in water (100 mL) and stirred vigorously. The precipitate was collected, washed with water and dried to provide 4,5,6-trichloro-(N'-2-acetyl)pyridine-2-carbohydrazide (8 g, 28 mmol), mp 185–188° C.

19. Preparation of 2,3,4-Trichloro-6-(5-methyl-1,3,4-thiadiazol-2-yl)pyridine A mixture of 4,5,6-trichloro-(N'-2-acetyl)pyridine-2-carbohydrazide (4.0 g, 14 mmol), 2,4-bis(4-methoxyphenyl)-1,3-dithia-2,4-diphosphetane-2,4-disulfide (Lawesson's Reagent, 5.73 g, 14 mmol) in toluene (50 mL)

was heated at 90° C. overnight. After cooling to room temperature, the insoluble precipitate was removed by suction filtration and the filtrate was concentrated. The residue was partitioned between ethyl acetate (100 mL) and water (100 mL), and the organic fraction was dried ($Na_2SO_4$), filtered and rotary evaporated to provide impure product (4 g). Precipitated material from the aqueous wash was collected by suction filtration and combined with the impure product and purified by column chromatography (0–100% ethyl acetate in hexane) to provide 2,3,4-trichloro-6-(5-methyl-1,3,4-thiadiazol-2-yl)pyridine (1.59 g, 5.7 mmol), mp 148–150° C.

20. Preparation of N-(2-Hydroxyphenyl)-4-amino-5,6-dichloropyridine-2-carboxamide A solution of 4,5,6-trichloropyridine-2-carbonyl chloride (1.0 g, 4.1 mmol) in dichloromethane (10 mL) was added dropwise to a solution of 2-aminophenol (0.45 g, 4.1 mmol) and triethylamine (0.6 mL) in dichloromethane (30 mL) at 0° C. The reaction mixture was allowed to warm to room temperature and stirred for an additional thirty minutes. The solvents were removed and the residue partitioned between 20% tetrahydrofuran/ethyl acetate and 1M hydrochloric acid. The organic layer was separated, washed with saturated sodium bicarbonate, brine, dried ($MgSO_4$) and concentrated to provide N-(2-hydroxyphenyl)-4,5,6-trichloropyridine-2-carboxamide (1.26 g, 4.0 mmol), mp 240° C. (dec).

21. Preparation of 4-Amino-2,3-dichloro-6-(2-benzoxazolyl)Pyridine

A solution of N-(2-hydroxyphenyl)-4-amino-5,6-dichloropyridine-2-carboxamide (1.80 g, 5.7 mmol) (obtained from N-(2-hydroxyphenyl)-2-(4,5,6-trichloro)pyridinecarboxamide via azide formation followed by sodium borohydride reduction) and p-toluenesulfonic acid (0.2 g) in toluene (50 mL) was refluxed overnight under nitrogen with a Dean-Stark trap. After cooling, the reaction mixture was diluted with ethyl acetate and THF, and the organic mixture washed with saturated aqueous sodium bicarbonate. The organic layer was dried, concentrated, and the residue triturated with petroleum ether/diethyl ether to provide 4-amino-2,3-dichloro-6-(2-benzoxazolyl)pyridine (1.30 g, 4.6 mmol). $^1$H NMR (DMSO-$d_6$): δ 7.82 (d, 2H), 7.66 (s, 1H), 7.55–7.38 (m, 2H), 7.18 (br.s, 2H).

22. Preparation of 4,5,6-Trichloropyridine-2-carbothioamide

A mixture of 4, 5, 6-trichloropyridine-2-carboxamide (10.4 g, 46 mmol) and 2,4-bis(4-methoxyphenyl)-1,3-dithia-2,4-diphosphetane-2,4-disulfide (Lawesson's Reagent, 22.0 g, 54 mmol) in toluene (150 mL) was heated under reflux for two hours. The reaction mixture was cooled, diluted with water (250 mL) and extracted with ethyl acetate (2×150 mL). The organic phase was dried ($Na_2SO_4$) and concentrated. The residue was purified by column chromatography (20% ethyl acetate in hexanes) to give 4, 5, 6-trichloropyridine-2-carbothioamide (6.5 g, 27 mmol): mp 168–169° C.

23. Preparation of 2,3,4-trichloro-6-[5-(trifluoromethyl)-1,3-thiazol-2-yl]pyridine and 2.3,4-trichloro-6-(4-(trifluoromethyl)-1,3-thiazol-2-yl)pyridine A mixture of 4, 5, 6-trichloropyridine-2-carbothioamide (2.85 g, 11.8 mmol) and 1-chloro-3,3,3-trifluoroacetone (2.59 g, 17.7 mmol) in glacial acetic acid (25 mL) was heated at reflux for 4 hours. Upon cooling, the solids formed were filtered and washed with water (3×100 mL) and sodium bicarbonate (3×50 mL). The solids were then dissolved in dichloromethane and the organic phase was washed with brine (150 mL), and dried ($MgSO_4$). The solvent was removed and the residue purified by preparative liquid chromatography (90% acetonitrile in water) to give 2,3,4-trichloro-6-[5-(trifluoromethyl)-1,3-thiazol-2-yl] pyridine (0.70 g, 2.1 mmol); $^1$H NMR (CDCl$_3$) δ 7.91 (s, 1H); 8.29 (s, 1H) and give 2,3,4-trichloro-6-[4-(trifluoromethyl)-1,3-thiazol-2-yl]pyridine (0.20 g, 0.6 mmol); $^1$H NMR (CDCl$_3$) δ 8.24 (1H, s), 8.39 (1H, s).

24. Preparation of Methyl 4-amino-3,6-dichloro-5-fluoropyridine-2-carboxylate

A solution of 4-amino-3,6-dichloropyridine-2-carboxylic acid (1100 g, 5.31 mol), 1-chloromethyl-4-fluoro-1,4-diazoniabicyclo[2.2.2]octane-bis(tetrafluoroborate) (2100 g, 5.93 mol) in water (6000 mL) was warmed to 65° C. for six hours. After cooling to ambient temperature, the reaction mixture was stirred an additional eighteen hours. The solution was concentrated and the resulting solid washed with 6 N hydrochloric acid (5×1000 mL) and dried to give 4-amino-3, 6-dichloro-5-fluoropyridine-2-carboxylic acid (757 g, 3.53 mol. 58% purity). This crude material was added to methanol (3000 ML) which had been saturated with anhydrous hydrogen chloride and the reaction mixture was warmed to 45° C. for two hours. The solution was added with vigorous stirring to ice water (4000 mL) and the resulting solid collected. The crude ester was dissolved in ethyl acetate (1000 mL) and washed with saturated sodium bicarbonate solution (2×1000 mL), dried, and concentrated. The resulting solid was recrystallized from ethyl acetate/hexanes to give methyl 4-amino-3,6-dichloro-5-fluoropyridine-2-carboxylate (402.5 g, 1.67 mol), mp 128–131° C.

25. Preparation of Methyl 4-amino-3-chloro-6-(3,4-dimethylphenyl)pyidine-2-carboxylate (Compound 12)

A solution of 3,4-dimethylphenylboronic acid (2.1 g, 14.0 mmol), cesium fluoride (6.3 g, 41.5 mmol), 1,4-bis(diphenylphosphino)butane (0.5 g, 1.2 mmol), methyl 4-amino-3,6-dichloropyridine-2-carboxylate (2.5 g, 10.0 mmol) and triethylamine (5 mL) in acetonitrile (100 mL) was sparged for thirty minutes with nitrogen. Palladium acetate (0.3 g, 1.2 mmol) was added and the reaction mixture heated under reflux for three hours. After cooling water (200 mL) was added and the mixture extracted with ethyl acetate (2×100 mL). The organic layer was washed with brine (100 mL), dried (NaSO$_4$), and concentrated. The residue was purified by column chromatography (33 percent ethyl acetate in hexane) to give methyl 4-amino-3-chloro-6-(3,4-dimethylphenyl)pyridine-2-carboxylate (1.4 g, 5.0 mmol), mp 154–156° C.

The following 4-amino-6-(aryl or heteroaryl)picolinates were prepared according to the procedure of Example 25:

Methyl 4-amino-3-chloro-6-(2,4-dichlorophenyl)pyridine-2-carboxylate (Compound 13): mp 130–31° C.

Methyl 4-amino-3-chloro-5-fluoro-6-(4-chlorophenyl)pyridine-2-carboxylate (Compound 14): mp 233–6° C.

Methyl 4-amino-3, 5-dichloro-6-(4-methoxyphenyl)pyridine-2-carboxylate (Compound 15): mp 107–9° C.

Methyl 4-amino-3-chloro-6-phenylpyridine-2-carboxylate (Compound 16): $^1$NMR (CDCl$_3$): δ 7.9 (d, 2H), 7.5 (m, 3H), 7.1 (s, 1H), 4.8 (br.s, 2H), 4.0 (s, 3H), Methyl 4-amino-3-chloro-6-(4-methoxyphenyl)pyridine-2-carboxylate (Compound 17): mp 148–49° C.

Methyl 4-amino-6-(4-methylphenyl)-3-(trifluoromethyl)pyridine-2-carboxylate (Compound 18): $^1$H NMR (CDCl$_3$): δ 7.85 (d, 2H), 7.25 (d, 2H), 7.00 (s, 1H), 4.90 (br.s, 2H), 3.95 (s, 3H), 2.40 (s,3H).

Methyl 4-amino-3-chloro-6-(4-chlorophenyl)pyridine-2-carboxylate (Compound 19): mp 132° C.

Methyl 4-amino-3-chloro-6-(4-methylphenyl)pyridine-2-carboxylate (Compound 20): mp 111–13° C.

Methyl 4-amino-3-chloro-6-(3-methylphenyl)pyridine-2-carboxylate (Compound 21): mp 98° C.

Methyl 4-amino-3-chloro-6-(4-thiomethoxyphenyl)pyridine-2-carboxylate (Compound 22): mp 185° C.

Methyl 4-amino-3-chloro-6-(2-methoxyphenyl)pyridine-2-carboxylate (Compound 23): $^1$H NMR (CDCl$_3$): δ 67.80 (m, 1H), 7.30 (m, 1H), 7.20 (s, 1H) 6.95 (m, 2H), 4.80 (br.s, 1H), 4.00 (s, 3H), 3.80 (s, 3H).

Methyl 4-amino-3-chloro-6-(3-methoxyphenyl)pyridine-2-carboxylate (Compound 24): mp 122–3° C.

Methyl 4-amino-3-chloro-6-(2-methylphenyl)pyridine-2-carboxylate (Compound 25): $^1$H NMR (CDCl$_3$): δ 7.30 (m, 4H), 6.70 (s, 1H), 4.90 (br.s, 2H), 4.00 (s, 3H), 2.35 (s, 3H).

Methyl 4-amino-3-chloro-6-(2-chlorophenyl)pyridine-2-carboxylate (Compound 26): mp 115–17° C.

Methyl 4-amino-3-chloro-6-(3-chlorophenyl)pyridine-2-carboxylate (Compound 27): mp 141° C.

Methyl 4-amino-3-chloro-6-[4-(trifluoromethyl)phenyl]pyridine-2-carboxylate (Compound 28): mp 149° C.

Methyl 4-amino-3-chloro-6-(3,4-methylenedioxyphenyl)pyridine-2-carboxylate (Compound 29): mp 184° C.

Methyl 4-amino-3-chloro-6-(4-ethylphenyl)pyridine-2-carboxylate (Compound 30): mp 119° C.

Methyl 4-amino-3-chloro-6-(4-acetylphenyl)pyridine-2-carboxylate (Compound 31): mp 146–48°C.

Methyl 4-amino-3-chloro-6-(5-bromo-2-methoxyphenyl)pyridine-2-carboxylate (Compound 32): mp 191–2° C.

Methyl 4-amino-3-chloro-6-(2-fluorophenyl)pyridine-2-carboxylate (Compound 33): mp 121–2° C.

Methyl 4-amino-3-chloro-6-(3,5-difluorophenyl)pyridine-2-carboxylate (Compound 34): mp 118–19° C.

Methyl 4-amino-3-chloro-6-(4-isopropylphenyl)pyridine-2-carboxylate (Compound 35): mp 92–93° C.

Methyl 4-amino-3-chloro-6-(4-biphenyl)pyridine-2-carboxylate (Compound 36): mp 185–6° C.

Methyl 4-amino-3-chloro-6-(2-fluorophenyl)pyridine-2-carboxylate (Compound 37): mp 121–2° C.

Methyl 4-amino-3-chloro-6-(4-chloro-3-methylphenyl)pyridine-2-carboxylate (Compound 38): mp 155–6° C.

Methyl 4-amino-3-chloro-6-(3-chloro-4-fluorophenyl)pyridine-2-carboxylate (Compound 39): mp 169–70° C.

Methyl 4-amino-3-chloro-6-(3,4-dichlorophenyl)pyridine-2-carboxylate (Compound 40): mp 170° C.

Methyl 4-amino-3-chloro-6-(4-formylphenyl)pyridine-2-carboxylate (Compound 41): mp 106–8° C.

Methyl 4-amino-3-chloro-6-(3-cyanophenyl)pyridine-2-carboxylate (Compound 42): mp 139–40° C.

Methyl 4-amino-3-chloro-6-(4-fluorophenyl)pyridine-2-carboxylate (Compound 43): mp 125° C.

Methyl 4-amino-3,5-dichloro-6-[4-(trifluoromethyl)phenyl]pyridine-2-carboxylate (Compound 44): mp 110–11° C.

Methyl 4-amino-3-chloro-6-(4-chloro-2-methylphenyl)pyridine-2-carboxylate (Compound 45): mp 114–15° C.

Methyl 4-amino-3-chloro-6-(3,5-bis-(trifluoromethyl)phenyl)pyridine-2-carboxylate (Compound 46): mp 139–40° C.

Methyl 4-amino-3-chloro-6-(2-naphthyl)pyridine-2-carboxylate (Compound 47): mp 108–09° C.

Methyl 4-amino-3-chloro-5-fluoro-6-(4-methylphenyl)-pyridine-2-carboxylate (Compound 48): $^1$H NMR (CDCl$_3$): δ 7.80 (d, 2H), 7.25 (d, 2H), 4.90 (br.s, 2H), 4.00 (s, 3H), 2.40 (s, 3H).

Methyl 4-acetamido-3-chloro-5-fluoro-6-(2,4-dichlorophenyl)pyridine-2-carboxylate (Compound 49): mp 178–79° C.

Methyl 4-amino-3-chloro-6-(3,4-difluoromethylenedioxyphenyl)pyridine-2-carboxylate (Compound 50): mp 130–132° C.

Methyl 4-amino-3-chloro-6-(3,5-difluorophenyl)pyridine-2-carboxylate (Compound 51): mp 155° C.

Methyl 4-acetamido-3-chloro-6-(4-chloro-2-fluorophenyl)pyridine-2-carboxylate (Compound 52): mp 134–35° C.

Methyl 4-acetamido-3-chloro-6-(4-chlorophenyl)pyridine-2-carboxylate (Compound 53): mp 151–52° C.

Methyl 4-acetamido-3-chloro-6-(2-chloro-4-fluorophenyl)pyridine-2-carboxylate (Compound 54): mp 162–63° C.

Methyl 4-acetamido-3-chloro-6-(2,6-difluorophenyl)pyridine-2-carboxylate (Compound 55): mp 156–57° C.

Methyl 4-amino-3-chloro-6-[4-(trifluoromethoxy)phenyl]pyridine-2-carboxylate (Compound 56): mp 119–20° C.

Methyl 4-acetamido-3-chloro-6-(2,5-dichlorophenyl)pyridine-2-carboxylate (Compound 57): mp 143° C.

Methyl 4-amino-3-chloro-6-(2-chloro-4-fluorophenyl)pyridine-2-carboxylate (Compound 58): mp 155–57° C.

Methyl 4-amino-3-chloro-6-(4-chloro-2-fluorophenyl)pyridine-2-carboxylate (Compound 59): mp 107–09° C.

Methyl 4-acetamido-3-chloro-6-(4-chloro-3-fluorophenyl)pyridine-2-carboxylate (Compound 60): mp 156–57° C.

Methyl 4-amino-3-chloro-6-(4-chloro-3-fluorophenyl)pyridine-2-carboxylate (Compound 61): mp 149–51° C.

Methyl 4-amino-3-chloro-6-[2-chloro-4-(trifluoromethyl)phenyl]pyridine-2-carboxylate (Compound 62): $^1$H NMR (CDCl$_3$): δ 7.70 (m, 2H), 7.60 (m, 1H), 7.05 (s, 1H), 4.90 (bs, 2H), 4.00 (s, 3H)

Methyl 4-acetamido-3-chloro-6-(3,4-dimethoxyphenyl)pyridine-2-carboxylate (Compound 63): mp 153–154° C.

Methyl 4-amino-3-chloro-6-(3,4-dimethoxyphenyl)pyridine-2-carboxylate (Compound 64): mp 126–27° C.

Methyl 4-amino-3-chloro-5-fluoro-6-(4-chlorophenyl)pyridine-2-carboxylate (Compound 65): mp 233–36° C.

Methyl 4-acetamido-3-chloro-6-(4-chloro-2-methoxyphenyl)pyridine-2-carboxylate (Compound 66): mp 176–78° C.

Methyl 4-amino-3-chloro-6-(3,4-ethylenedioxyphenyl)pyridine-2-carboxylate (Compound 67): $^1$H NMR (CDCl$_3$): δ 7.50 (d, 1H), 6.40 (m, 1H), 7.05 (s, 1H), 6.90 (d, 1H) 4.80 (br.s, 2H), 4.30 (s, 4H), 4.00 (s, 3H).

Methyl 4-amino-3-chloro-6-(4-chloro-2-methoxyphenyl)pyridine-2-carboxylate (Compound 68): mp 152–54° C.

Methyl 4-acetamido-3-chloro-6-(3,4-methylenedioxyphenyl)pyridine-2-carboxylate (Compound 69): $^1$H NMR (DMSO-d$_6$): 7.40 (m, 2H), 7.20 (s, 1H), 7.10 (m, 1H), 6.70 (br.s, 2H), 6.10 (s, 2H), 3.90 (s, 3H).

Methyl 4-acetamido-3-chloro-6-(4-chloro-3-methoxymethylphenyl)pyridine-2-carboxylate (Compound 70): mp 120–22° C.

Methyl 4-amino-3-chloro-6-(4-chloro-3-methoxymethylphenyl)pyridine-2-carboxylate (Compound 71): mp 73–74° C.

Methyl 4-acetamido-3-chloro-6-(2-chloro-3,4-methylenedioxyphenyl)pyridine-2-carboxylate (Compound 72): mp 195–96° C.

Methyl 4-amino-3-chloro-6-(2-chloro-3,4-methylenedioxyphenyl)pyridine-2-carboxylate (Compound 73): mp 155–56° C.

Methyl 4-acetamido-3-chloro-6-(5-indanyl)pyridine-2-carboxylate (Compound 74): mp 132–34° C.

Methyl 4-amino-3-chloro-6-(5-indanyl)pyridine-2-carboxylate (Compound 75): mp 165–66° C.

Methyl 4-acetamido-3-chloro-6-(2,3-dihydro-5-benzofuranyl)pyridine-2-carboxylate (Compound 76): $^1$H NMR (CDCl$_3$): δ 8.90 (s, 1H), 8.45 (s, 1H), 7.90 (s, 1H), 7.78 (d, 1H), 6.85 (d, 1H), 4.65 (t, 2H), 4.00 (s, 3H), 3.25 (t, 3H) 2.30 (s, 3H).

Methyl 4-amino-3-chloro-6-(2,3-dihydro-5-benzofuranyl) pyridine-2-carboxylate (Compound 77): mp 143° C.

Methyl 4-acetamido-3-chloro-6-(5-chloro-2-fluoro-4-methylphenyl)pyridine-2-carboxylate (Compound 78): mp 187–5° C.

Methyl 4-amino-3-chloro-6-(5-chloro-2-fluoro-4-methylphenyl)pyridine-2-carboxylate (Compound 79): mp 108–10° C.

Methyl 4-amino-3-chloro-6-(4-methoxy-3-methylphenyl) pyridine-2-carboxylate (Compound 80): mp 158° C.

Methyl 4-acetamido-3-chloro-6-(2,5-dimethoxyphenyl) pyridine-2-carboxylate (Compound 81): mp 124–25° C.

Methyl 4-amino-3-chloro-6-(2,5-dimethoxyphenyl) pyridine-2-carboxylate (Compound 82): $^1$NMR (CDCl$_3$): δ 7.40 (d, 1H), 7.30 (s, 1H), 6.95 (m, 1H), 4.80 (br.s, 2H), 4.00 (s, 3H), 3.85 (s, 3H), 3.80 (s, 3H).

Methyl 4-acetamido-3-chloro-6-(4-methylphenyl)pyridine-2-carboxylate (Compound 83): mp 156° C.

Methyl 4-amino-3-chloro-5-fluoro-6-(3,4-methylenedioxyphenyl)pyridine-2-carboxylate (Compound 84): mp 160° C.

Methyl 4-amino-3-chloro-5-fluoro-6-(2,3-dihydro-5-benzofuranyl)pyridine-2-carboxylate (Compound 85): mp 120° C.

Methyl 4-amino-3,5-dichloro-6-(4-chlorophenyl)pyridine-2-carboxylate (Compound 86): mp 160–62° C.

Methyl 4-acetamido-3-chloro-6-(1-methyl-1H-pyrazol-4-yl)pyridine-2-carboxylate (Compound 87): mp 177–78° C.

Methyl 4-amino-3-chloro-5-fluoro-6-(2,4-dichlorophenyl) pyridine-2-carboxylate (Compound 88): mp 122° C.

Methyl 4-N-pyrolyl-3-chloro-6-(4-methylphenyl)pyridine-2-carboxylate (Compound 89): mp 118–19° C.

Methyl 4-amino-3,5-difluoro-6-(4-chlorophenyl)pyridine-2-carboxylate (Compound 90): mp 165–66° C.

Methyl 4-amino-3,5-difluoro-6-(4-methylphenyl)pyridine-2-carboxylate (Compound 91): mp 145–46° C.

Methyl 4-amino-3,5-difluoro-6-(2-chloro-4-methylphenyl) pyridine-2-carboxylate (Compound 92): $^1$H NMR (CDCl$_3$): δ 7.30 (m, 2H), 7.15 (m, 1H), 4.60 (bs, 2H), 4.00 (s, 3H), 2.40 (s, 3H).

Methyl 4-amino-3,5-difluoro-6-(4-chloro-2-fluorophenyl) pyridine-2-carboxylate (Compound 93): mp 182–83° C.

Methyl 4-amino-3,5-difluoro-6-[4-(trifluoromethyl)phenyl] pyridine-2-carboxylate (Compound 94): mp 177–78° C.

Methyl 4-amino-3,5-difluoro-6-(3,4-methylenedioxyphenyl)pyridine-2-carboxylate (Compound 95): mp 189–90° C.

Methyl 4-amino-3-chloro-6-(2-benzofuranyl)pyridine-2-carboxylate (Compound 96): mp 182–183° C.

Methyl 4-acetamido-3-chloro-6-(2-benzothienyl)pyridine-2-carboxylate (Compound 97): mp 184–185° C.

Methyl 4-amino-3-chloro-6-(5-chloro-2-thienyl)pyridine-2-carboxylate (Compound 98): $^1$H NMR (CDCl$_3$): δ 7.40 (d, 1H), 7.20 (m, 2H), 6.80 (br.s, 2H), 3.90 (s, 3H).

Methyl 4-acetamido-6-(2-benzofuranyl)-3-chloropyridine-2-carboxylate (Compound 99): $^1$H NMR (DMSO-d$_6$): δ 10.00 (br.s, 1H), 8.80 (s, 1H), 8.25 (s, 3H), 7.70 (m, 1H), 7.60 (s, 1H) 7.40 (m, 2H), 7.60 (s, 1H), 4.00 (s, 3H) 2.25 (s, 3H).

Methyl 4-amino-3-chloro-6-(3,5-dimethyl-4-isoxazolyl) pyridine-2-carboxylate (Compound 100): mp 143° C.

Methyl 4-acetamido-3-chloro-6-(3-thienyl)pyridine-2-carboxylate (Compound 101): mp 133° C.

11091454 Methyl 4-amino-3-chloro-6-(3-pyridyl)pyridine-2-carboxylate, (Compound 102): mp 144–146° C.

26. Preparation of Methyl 4-acetamido-3-chloro-6-(2-thiazolyl)pyridine-2-carboxylate (Compound 103)

A solution of methyl 4-acetamido-3,6-dichloropyridine-2-carboxylate (1.0 g, 4.05 mmol), 2-(trimethylstannyl) thiazole (2.9 g, 17.3 mmol) and dichlorobis (triphenylphosphine)palladium(II) (0.4 g, 0.6 mmol) in tetrahydrofuran (75 mL) was heated under reflux for four hours. The reaction was diluted with water (100 mL) and extracted with ethyl acetate (2×100 mL). The organic phase was dried (MgSO$_4$) and concentrated. The crude product was purified by column chromatography (50% ethyl acetate in hexane) to give methyl 4-acetamido-3-chloro-6-(2-thiazolyl)pyridine-2-carboxylate (0.38 g, 1.2 mmol), mp 187–8° C.

The following 4-amino-6-(aryl or heteroaryl)picolinates were prepared according to the procedure of Example 26:

Methyl 4-amino-3,5-dichloro-6-(2-furanyl)pyridine-2-carboxylate (Compound 104): mp 116–17° C.

Methyl 4-amino-3,5-dichloro-6-(2-thienyl)pyridine-2-carboxylate (Compound 105): mp 132° C.

Methyl 4-amino-3-chloro-6-(2-thienyl)pyridine-2-carboxylate (Compound 106): mp 138–9° C.

Methyl 4-amino-3-chloro-6-(6-methoxy-4-pyridinyl) pyridine-2-carboxylate (Compound 107): mp 185–87° C.

Methyl 4-amino-3-chloro-6-(6-hydroxy-3-pyridinyl) pyridine-2-carboxylate (Compound 108): mp 251–52° C.

Methyl 4-amino-3-chloro-6-(2-pyridinyl)pyridine-2-carboxylate (Compound 109): mp 142–45° C.

Methyl 4-amino-3-chloro-6-(2-furanyl)pyridine-2-carboxylate (Compound 110): mp 117° C.

Methyl 4-amino-3-chloro-6-(5-chloro-2-pyridyl)pyridine-2-carboxylate, (Compound 111): mp 145–50° C.

Methyl 4-acetamido-3-chloro-6-(3-(6-methyl)pyridazyl) pyridine-2-carboxylate (Compound 112): mp 205–206° C.

Methyl 4-amino-3-chloro-5-fluoro-6-(2-thiazolyl)pyridine-2-carboxylate (Compound 113): mp 185–187° C.

Methyl 4-amino-3-chloro-6-(2-(5-methylthiazolyl)) pyridine-2-carboxylate (Compound 114): mp 186–188° C.

Methyl 4-amino-3,5-dichloro-6-(5-thiazolyl))pyridine-2-carboxylate (Compound 115): mp 168–170° C.

27. Preparation of Methyl 4-acetamido-3-chloro-6-(trimethylstannyl)pyridine-2-carboxylate A solution of methyl 4-acetamido-3,6-dichloropyridine-2-carboxylate (5.00 g, 19.0 mmol), 1,4-bis (diphenylphosphino) butane (0.81 g, 1.9 mmol) and hexamethylditin (6.22 g, 19.0 mmol) in dioxane (150 mL) was sparged with nitrogen for 15 minutes. Palladium acetate (0.43 g, 1.9 mmol) was then added and the mixture refluxed for 3 hours. After filtration through Celite the reaction mixture was concentrated. The residue was taken up into ethyl acetate and washed three times with water. The organic layer was dried, concentrated, and taken up into an ethyl acetate/hexane (1:1) mixture. Solid impurities were filtered off and the solvents removed to yield methyl 4-acetamido-3-chloro-6-(trimethylstannyl)pyridine-2-carboxylate (4.25 g, 10.9 mmol), 113–115° C.

28. Preparation of Methyl 4-acetamido-3-chloro-6-(5-(2-chloro)pyrimidinyl)-pyridine-2-carboxylate (Compound 116)

A solution of methyl 4-acetamido-3-chloro-6-(trimethylstannyl)-pyridine-2-carboxylate (1.00 g, 2.60 mmol), 1,4-bis(diphenylphosphino)butane (0.12 g, 0.29 mmol) and 5-bromo-2-chloropyrimidine (0.25 g, 1.30 mmol) in dioxane (30 mL) was sparged with nitrogen for 15 minutes. Palladium acetate (0.07 g, 0.29 mmol) was then added and the mixture refluxed for 3 hours. After filtration through celite the reaction mixture was concentrated. The residue was taken up into ethyl acetate and washed three times with water. The organic layer was dried, concentrated, and column chromatography (50% ethyl acetate in hexane) provided methyl 4-acetamido-3-chloro-6-(5-(2-chloro) pyrimidinyl)pyridine-2-carboxylate (0.120 g, 0.35 mmol). $^1$H NMR (CDCl$_3$) δ 9.22 (s, 2H), 9.08 (s, 1H), 8.03 (br.s, 1H), 4.05 (s, 3H), 2.37 (s, 3H).

The following compound was prepared according to the procedure of Example 28:

Methyl 4-acetamido-3-chloro-6-(5-pyrimidinyl)pyridine-2-carboxylate (Compound 117): mp 178–185° C.

Methyl 4-acetamido-3-chloro-6-(3-(6-methyl)pyridazinyl)pyridine-2-carboxylate (Compound 118): mp 205–206° C.

29. Preparation of Methyl 6-acetylene-3,4-dichloropyridine-2-carboxylate

Copper(I) iodide (0.16 g, 0.84 mmol) was stirred in triethylamine at 75° C. for 10 minutes and then cooled to room temperature. Trimethylsilylacetylene (0.40 mL, 2.8 mmol) was then added and the mixture stirred for 10 minutes, followed by dichlorobis(triphenyl-phosphine) palladium(II) (0.30 g, 0.43 mmol). After an additional 10 minutes, a solution of methyl 3,4,6-trichloropyridine-2-carboxylate (2.00 g, 8.30 mmol) in triethylamine (10 mL) was added. A second portion of trimethylsilylacetylene (1.40 mL, 10 mmol) was further added and the mixture was warmed in an oil bath to 90° C. After 15 minutes, the reaction mixture was cooled, filtered through diatomaceous earth, and concentrated. The crude reaction product was then eluted through a short silica gel column (25% ethyl acetate in hexane) to provide 2.20 g (7.30 mmol) of crude methyl 3,4-dichloro-6-trimethylsilylacetylenepyridine-2-carboxylate. This material was taken up into tetrahydrofuran (50 mL), cooled to −20° C., and was treated with 1M tetrabutylammonium fluoride in THF (8.0 mL, 8.0 mmol). Within minutes, the crude mixture was poured onto ice, extracted with diethyl ether, dried (MgSO$_4$), filtered and evaporated to yield a black solid. Purification by column chromatography (25% ethyl acetate in hexane) gave methyl 6-acetylene-3,4-dichloropyridine-2-carboxylate (1.22 g, 5.30 mmol): $^1$H NMR (CDCl$_3$) δ 7.70 (s, 1H), 4.02 (s, 3H), 3.31 (s, 1H).

The following compound was prepared according to the procedure of Example 29:

Methyl 4-acetamido-6-acetylene-3-chloropyridine-2-carboxylate: $^1$H NMR (CDCl$_3$) δ 8.78 (s, 1H), 7.97 (br.s, 1H), 4.00 (s, 3H), 3.22 (s, 1H), 2.36 (s, 3H).

30. Preparation of Methyl 3,4-dichloro-6-(4-triazoyl)pyridine-2-carboxylate and Methyl 3-azido-4-chloro-6-(4-triazoyl)pyridine-2-carboxylate Methyl 6-acetylene-3,4-dichloropyridine-2-carboxylate (1.50 g, 6.50 mmol) was stirred with sodium azide (1.30 g, 19.50 mmol) in DMF (50 mL) at 50° C. After 16 hours, the reaction mixture was cooled to room temperature and partitioned between ethyl acetate and water (acidified with 1N hydrochloric acid). The organic layer was separated, dried (MgSO$_4$), filtered, and concentrated. The crude products were purified by reverse phase preparative liquid chromatography (40 to 70% acetonitrile in water) to yield methyl 3,4-dichloro-6-(4-triazoyl)-pyridine-2-carboxylate (0.35 g, 1.29 mmol); $^1$H NMR (CDCl$_3$) δ 8.35 (s, 1H), 8.28 (s, 1H), 4.07 (s, 3H) and methyl 3-azido-4-chloro-6-(4-triazoyl) pyridine-2-carboxylate (0.30 g, 1.10 mmol); $^1$H NMR (CDCl$_3$) δ 8.37 (s, 1H), 7.97 (s, 1H), 4.06 (s, 3H).

31. Preparation of Methyl 4-acetamido-3-chloro-6-(3-bromo-5-isoxazoyl)pyridine-2-carboxylate (Compound 119) and Methyl 4-acetamido-3-chloro-6-(3-bromo-4-isoxazoyl)pyridine-2-carboxylate (Compound 120)

A solution of dibromoformaldoxime (0.38 g, 1.87 mmol) in ethyl acetate (3 mL) was slowly added over 4 hours to a mixture of methyl 4-acetamido-6-acetylene-3-chloropyridine-2-carboxylate (0.70 g, 2.80 mmol) and potassium bicarbonate (0.37 g, 3.70 mmol) in ethyl acetate and water (0.4 mL). After stirring at ambient temperature for additional 16 hours, the crude reaction mixture was partitioned between ethyl acetate and water. The organic layer was separated, dried (MgSO$_4$), filtered, and concentrated. The products were purified by reverse phase preparative liquid chromatography (60% acetontrile in water with 0.5% phosphoric acid) to give starting methyl 4-acetamido-6-acetylene-3-chloropyridine-2-carboxylate (0.15 g, 0.06 mmol), methyl 4-acetamido-3-chloro-6-(3-bromo-5-isoxazoyl)pyridine-2-carboxylate (0.51 g, 1.37 mmol); $^1$H NMR (CDCl$_3$) δ 9.14 (s, 1H), 8.00 (br.s, 1H), 7.05 (s,1H), 4.05 (s, 3H), 2.37 (s, 3H) and methyl 4-acetamido-3-chloro-6-(3-bromo-4-isoxazoyl)pyridine-2-carboxylate (0.03 g, 0.08 mmol); $^1$H NMR (CDCl$_3$) δ 9.22 (s, 1H), 8.92 (br.s, 1H), 8.00 (s,1H), 4.02 (s, 3H), 2.34 (s, 3H).

32. Preparation of Methyl 3,4-dichloro-6-(2-methyl-3-pyrazoyl)pyridine-2-carboxylate Methyl 3,4-dichloro-6-(3-pyrazoyl)pyridine-2-carboxylate and Methyl 3,4-dichloro-6-(1-methyl-3-pyrazoyl)pyridine-2-carboxylate Trimethylsilyldiazomethane (2.0 M in hexanes, 10 mL, 20.0 mmol) was added to a solution of methyl 6-acetylene-3,4-dichloropyridine-2-carboxylate (1.70 g, 7.0 mmol) in ethyl acetate and methanol (1:1, 50 mL). After 4 hours, the reaction mixture was concentrated and the residue purified by column chromatography (25 to 50% ethyl acetate in petroleum ether) to yield methyl 3,4-dichloro-6-(2-methyl-3-pyrazoyl)pyridine-2-carboxylate (0.33 g, 1.15 mmol); $^1$H NMR (CDCl$_3$) δ 7.80 (s, 1H), 7.54 (d, J=2.0 Hz, 1H), 6.66 (d, J=2.0 Hz, 1H), 4.25 (s, 3H), 4.05 (s, 3H); methyl 3,4-dichloro-6-(3-pyrazoyl)pyridine-2-carboxylate (0.50 g, 1.84 mmol); $^1$H NMR (CDCl$_3$) δ 10.90 (br.s, 1H), 8.09 (s, 1H) 7.68 (d, J=2.2 Hz, 1H), 6.93 (d, J=2.2 Hz, 1H), 4.05 (s, 3H) and methyl 3,4-dichloro-6-(1-methyl-3-pyrazoyl)pyridine-2-carboxylate (0.08 g, 0.28 mmol); $^1$H NMR (CDCl$_3$) δ 8.14 (s, 1H), 7.40 (d, J=2.3 Hz, 1H), 6.89 (d, J=2.3 Hz, 1H), 4.25 (s, 3H), 3.96 (s, 3H).

33. Preparation of Methyl 4-amino-3-chloro-6-(3-(6-methyl)pyridazinyl)pyridine-2-carboxylate (Compound 121)

A solution of methyl 4-acetamido-3-chloro-6-(3-(6-methyl)pyridazinyl)pyridine-2-carboxylate (100 mg, 0.31 mmol) and sodium methoxide (17 mg, 0.31 mmol) in methanol (4 mL) was heated at reflux for 1 hour under an atmosphere of nitrogen. The heat was removed and the reaction mixture stirred at room temperature overnight. After the solvent was removed, the residue was taken up into ethyl actetate and washed with water, brine and dried (MgSO$_4$). Column chromatography (10% methanol in dichloromethane) yielded methyl 4-amino-3-chloro-6-(3-(6-methyl)pyridazinyl)pyridine-2-carboxylate (47 mg, 0.17 mmol), mp 210–11° C.

The following compounds were prepared according to the procedure in Example 33:

Methyl 4-amino-3-chloro-6-(3-thienyl)pyridine-2-carboxylate (Compound 122): mp 129° C.

Methyl 4-amino-3-chloro-6-(2-thiazolyl)pyridine-2-carboxylate (Compound 123): mp 195–97° C.

Methyl 4-amino-3-chloro-6-(1-methyl-1H-pyrazol-4-yl)pyridine-2-carboxylate (Compound 124): mp 174–76° C.

Methyl 4-amino-3-chloro-6-(2-benzothienyl)pyridine-2-carboxylate (Compound 125): mp 177–178° C.

Methyl 4-amino-3-chloro-6-(5-pyrimidinyl)pyridine-2-carboxylate (Compound 126): mp 195° C.

34. Preparation of Methyl 4-amino-3-chloro-6-(6-hydroxy-3-pyridinyl)pyridine-2-carboxylate (Compound 127)

Methyl 4-amino-3-chloro-6-(6-t-butoxy-3-pyridinyl)pyridine-2-carboxylate (0.50 g, 1.49 mmol) was dissolved in a 1:1 mixture of THF and trifluoroacetic acid (5 mL) and heated to reflux for 30 minutes. The volatiles were removed in vacuo and the crude material was purified by HPLC (linear gradient, 100% water to 100% acetonitrile) to give of methyl 4-amino-3-chloro-6-(6-hydroxy-3-pyridinyl)pyridine-2-carboxylate (0.35 g, 1.25 mmol): Mp 251-52° C.

35. Preparation of Methyl 4-amino-3-chloro-6-(6-chloro-3-pyridinyl)pyridine-2-carboxylate (Compound 128)

Methyl 4-amino-3-chloro-6-(6-hydroxy-3-pyridinyl)pyridine-2-carboxylate (0.30 g, 1.07 mmol) was suspended in neat dichlorophenylphosphine (2.5 mL, 1.84 mmol) and the mixture was heated to 50° C. for 1 hr. The volatiles were removed in vacuo and the residue purified by column chromatography (1:1, Hexanes/EtOAc) to give of methyl 4-amino-3-chloro-6-(6-chloro-3-pyridinyl)pyridine-2-carboxylate (0.11 g, 0.37 mmol).

36. Preparation of Methyl 14-amino-3-chloro-6-(4-(2-methylthiazolyl))-pyridine-2-carboxylate (Compound 129)

HCl gas was bubbled through a solution of methyl 4-acetamido-3-chloro-6-(4-(2-methylthiazolyl))-pyridine-2-carboxylate (100 mg, 0.31 mmol) for 2 minutes. The mixture was refluxed for 2 hours, cooled, and was concentrated. The residue was partitioned between methylene chloride and 1M ammonium hydroxide. The organic layer was separated off, dried (MgSO$_4$) and concentrated to give methyl 4-amino-3-chloro-6-(4-(2-methylthiazolyl))-pyridine-2-carboxylate (74 mg, 0.26 mmol): $^1$H NMR (CDCl$_3$) δ 7.94 (s, 1H), 7.58 (s, 1H), 4.97 (br.s, 2H), 4.02 (s, 3H), 2.77 (s, 3H).

The following compounds were prepared according to the procedure in Example 36:

Methyl 4-amino-3-chloro-6-(3-bromo-5-isoxazoyl))-pyridine-2-carboxylate (Compound 130): $^1$H NMR (CDCl$_3$) δ 7.29 (s, 1H), 6.98 (s, 1H), 5.00 (br.s, 1H), 4.00 (s, 3H).

Methyl 4-amino-3-chloro-6-(3-bromo-4-isoxazoyl))-pyridine-2-carboxylate (Compound 131): $^1$H NMR (CDCl$_3$) δ 8.88 (s, 1H), 7.28 (s, 1H), 4.90 (br.s, 1H), 4.00 (s, 3H).

37. Preparation of 4-amino-3-chloro-6-(3,4-dimethylphenyl)pyridine-2-carboxylic acid (Compound 132)

Methyl 4-amino-3-chloro-6-(3,4-dimethylphenyl)pyridine-2-carboxlate (0.9 g, 0.003 mol) was heated at reflux in methanol (50 mL) and 1N sodium hydroxide (75 mL) for two hours. The reaction mixture was partially concentrated and then acidified with concentrated hydrochloric acid. The solid was collected and dried to give 4-amino-3-chloro-6-(3,4-dimethylphenyl)-pyridine-2-carboxylic acid (0.85 g, 0.003 mol), mp 192–4° C.

The following acids were prepared according to the procedure in Example 37:

4-Amino-3,5-dichloro-6-(phenyl)pyridine-2-carboxylic acid (Compound 133): mp 135° C.

4-Amino-3,5-dichloro-6-(4-methoxyphenyl)pyridine-2-carboxylic acid (Compound 134): mp 139–40° C. dec.

4-Amino-3-chloro-6-(phenyl)pyridine-2-carboxylic acid (Compound 135): mp 180–81° C. dec.

4-Amino-3-chloro-6-(4-methylphenyl)pyridine-2-carboxylic acid (Compound 136): mp 166–67° C.

4-Amino-3-chloro-6-(4-thiomethylphenyl)pyridine-2-carboxylic acid (Compound 137): mp 173–35° C.

4-Amino-3-chloro-6-(3-methylphenyl)pyridine-2-carboxylic acid (Compound 138): mp 173–75° C.

4-Amino-3-chloro-6-(2-methoxyphenyl)pyridine-2-carboxylic acid (Compound 139): mp 177–79° C.

4-Amino-3-chloro-6-(2-chlorophenyl)pyridine-2-carboxylic acid (Compound 140): mp 196–7° C.

4-Amino-3-chloro-6-(4-methoxyphenyl)pyridine-2-carboxylic acid (Compound 141): $^1$H NMR (DMSO-d$_6$): δ 7.82 (d, J=8.8 Hz, 2H), 7.20 (s, 1H), 7.00 (d, J=8.8 Hz, 2H), 6.64 (s, 2H), 6.52 (s, 1H), 3.78 (s, 3H).4-Amino-3-chloro-6-(2-fluorophenyl)pyridine-2-carboxylic acid (Compound 142): mp 192° C.

4-Amino-3-chloro-6-(3-chlorophenyl)pyridine-2-carboxylic acid (Compound 143): mp 171° C.

4-Amino-3-chloro-6-(4-acetylphenyl)pyridine-2-carboxylic acid (Compound 144): mp 177–78° C.

4-Amino-3-chloro-6-(2,4-difluorophenyl)pyridine-2-carboxylic acid (Compound 145): mp 206° C. dec.

4-Amino-3-chloro-6-(2,4-dichlorophenyl)pyridine-2-carboxylic acid (Compound 146): mp 176–77° C.

4-Amino-3-chloro-6-(4-isopropylphenyl)pyridine-2-carboxylic acid (Compound 147): mp 142–143° C.

4-Amino-3-chloro-6-(4-biphenyl)pyridine-2-carboxylic acid (Compound 148): mp 300–05° C.

4-Amino-3-chloro-6-(4-chloro-3-methylphenyl)pyridine-2-carboxylic acid (Compound 149): mp 190–91° C.

4-Amino-3-chloro-6-(3,4-dichlorophenyl)pyridine-2-carboxylic acid (Compound 150): mp 185–86° C.

4-Amino-3-chloro-6-(3-chloro-4-fluorophenyl)pyridine-2-carboxylic acid (Compound 151): mp, 183–84° C.

4-Amino-3-chloro-6-[4-(trifluoromethyl)phenyl]pyridine-2-carboxylic acid (Compound 152): mp 175–76° C.

4-Amino-3-chloro-6-(3,4-methylenedioxyphenyl)pyridine-2-carboxylic acid (Compound 153): mp 182° C.

4-Amino-3-chloro-6-(4-chlorophenyl)pyridine-2-carboxylic acid (Compound 154): mp 165° C.

4-Amino-3-chloro-6-(4-chloro-2-methylphenyl)pyridine-2-carboxylic acid (Compound 155): mp 153–154° C.

4-Amino-3-chloro-6-(4-fluorophenyl)pyridine-2-carboxylic acid (Compound 156): mp 170–71° C.

4-Amino-3-chloro-6-[3-(trifluoromethyl)phenyl]pyridine-2-carboxylic acid (Compound 157): mp 175–76° C.

4-Amino-3-chloro-6-(2-fluoro-4-methylphenyl)pyridine-2-carboxylic acid (Compound 158): mp 187–89° C.

4-Amino-3-chloro-6-(4-hydroxymethylphenyl)pyridine-2-carboxylic acid (Compound 159): mp 181–2° C.

4-Amino-3-chloro-6-[4-(fluoromethyl)phenyl]pyridine-2-carboxylic acid (Compound 160): mp 156–57° C.

4-Amino-3-chloro-6-[bis-3,5-(trifluoromethyl)phenyl]pyridine-2-carboxylic acid (Compound 161): mp 184° C.

4-Amino-3-chloro-6-(2-napthyl)pyridine-2-carboxylic acid (Compound 162): mp 168–69° C.

4-Amino-3-chloro-5-fluoro-6-(4-methylphenyl)pyridine-2-carboxylic acid (Compound 163): mp 145–48° C dec.

4-Amino-3-chloro-6-(3-chloro-4-methylphenyl)pyridine-2-carboxylic acid (Compound 164): mp 188° C.

4-Amino-3-chloro-6-(2-methylphenyl)pyridine-2-carboxylic acid (Compound 165): mp 188–89° C.

4-Amino-3-chloro-6-(3,4-difluoromethylenedioxyphenyl)pyridine-2-carboxylic acid (Compound 166): mp 170° C.

4-Amino-3-chloro-6-(3,5-difluorophenyl)pyridine-2-carboxylic acid (Compound 167): mp 182–83° C.

4-Amino-3-chloro-6-(4-chloro-2-fluorophenyl)pyridine-2-carboxylic acid (Compound 168): mp 162–63° C.

4-Amino-3-chloro-6-(2,6-difluorophenyl)pyridine-2-carboxylic acid (Compound 169): mp 165–66° C.

4-Amino-3-chloro-6-(2-chloro-4-fluorophenyl)pyridine-2-carboxylic acid (Compound 170): mp 156–57° C.
4-Amino-3',5-dichloro-6-[4-(trifluoromethyl)phenyl]pyridine-2-carboxylic acid (Compound 171): mp 158–60° C.
4-Amino-3-chloro-5-fluoro-6-(4-trifluorophenyl)pyridine-2-carboxylic acid (Compound 172): mp 137–38° C.
4-Amino-3-chloro-5-fluoro-6-(4-chlorophenyl)pyridine-2-carboxylic acid (Compound 173): mp 164–65° C.
4-Amino-3-chloro-6-[4-(trifluoromethoxy)phenyl]pyridine-2-carboxylic acid (Compound 174): mp 164–65° C.
4-Amino-3-chloro-6-(4-ethylphenyl)pyridine-2-carboxylic acid (Compound 175): mp 152° C.
4-Amino-3-chloro-6-(2-fluorophenyl)pyridine-2-carboxylic acid (Compound 176): mp 121–2° C.
4-Amino-3-chloro-6-(2,5-dichlorophenyl)pyridine-2-carboxylic acid (Compound 177): mp 213–215° C.
4-Amino-3-chloro-6-(2,4-dimethylphenyl)pyridine-2-carboxylic acid (Compound 178): $^1$H NMR (DMSO-$d_6$): δ 7.25 (m, 1H), 7.15 (m, 2H), 6.8 (s, 1H), 6.70 (bs, 2H), 2.30 (s, 3H), 2.25 (s, 3H).
4-Amino-3-chloro-6-(4-chloro-3-(trifluoromethyl)phenyl)pyridine-2-carboxylic acid (Compound 179): mp 176° C.
3-chloro-6-(4-methylphenyl)-4-(N-pyrolyl)pyridine-2-carboxylic acid (Compound 180): mp 136–37° C.
4-Amino-3-chloro-6-(4-chloro-3-fluorophenyl)pyridine-2-carboxylic acid (Compound 181): mp 156–57° C.
4-Amino-3-chloro-6-(4-chloro-2-(trifluoromethyl)phenyl)pyridine-2-carboxylic acid (Compound 182): mp 178–80° C.
4-Amino-3-chloro-5-fluoro-6-(4-chlorophenyl)pyridine-2-carboxylic acid (Compound 183): mp. 169–70° C.
4-Amino-3-chloro-6-(2-chloro-4-(trifluoromethyl)phenyl)pyridine-2-carboxylic acid (Compound 184): $^1$H NMR (DMSO-$d_6$): δ 8.00 (s, 1H), 7.80 (m, 2H), 7.00 (s, 1H), 6.85 (br.s, 2H).
4-Amino-3-chloro-6-(3,4-dimethoxyphenyl)pyridine-2-carboxylic acid (Compound 185): mp 182–83° C.
4-Amino-3-chloro-6-(4-chloro-2-methoxyphenyl)pyridine-2-carboxylic acid (Compound 186): mp 182–83° C.
4-Amino-3-chloro-6-(2-chloro-3,4-methylenedioxyphenyl)pyridine-2-carboxylic acid (Compound 187): mp 226–27° C.
4-Amino-3-chloro-6-(5-indanyl)pyridine-2-carboxylic acid (Compound 188): mp 204–05° C.
4-Amino-3-chloro-5-fluoro-6-(4-chloro-2-fluorophenyl)pyridine-2-carboxylic acid (Compound 189): mp 154–5° C.
4-Amino-3-chloro-6-(2-chloro-4-methylphenyl)pyridine-2-carboxylic acid (Compound 190): mp 71–72° C.
4-Amino-3-chloro-6-(4-methyl-3-thiomethylphenyl)pyridine-2-carboxylic acid (Compound 191): mp 188–90° C.
4-Amino-3-chloro-6-(5-chloro-2-fluoro-4-methylphenyl)pyridine-2-carboxylic acid (Compound 192): mp 173–75° C.
4-Amino-3-chloro-6-(4-methoxy-3-methylphenyl)pyridine-2-carboxylic acid (Compound 193): mp 131° C.
4-Amino-3-chloro-6-(2,5-dimethoxyphenyl)pyridine-2-carboxylic acid (Compound 194): mp 185–86° C.
4-Amino-3-chloro-6-(4-chloro-3-methoxymethylphenyl)pyridine-2-carboxylic acid (Compound 195): mp 162° C.
4-Amino-3-chloro-5-fluoro-6-(3,4-methylenedioxyphenyl)pyridine-2-carboxylic acid (Compound 196): mp 169° C.
4-Amino-3-chloro-5-fluoro-6-(2,3-dihydro-5-benzofuranyl)pyridine-2-carboxylic acid (Compound 197): mp 171° C.
4-Amino-3,5-dichloro-6-(4-chlorophenyl)pyridine-2-carboxylic acid (Compound 198): mp 164–65° C.
4-Amino-3-chloro-5-fluoro-6-(2,4-dichlorophenyl)pyridine-2-carboxylic acid (Compound 199): mp 152° C.
4-Amino-3,5-fluoro-6-(4-(trifluoromethyl)phenyl)pyridine-2-carboxylic acid (Compound 200): mp 169–70° C.
4-Amino-3-chloro-6-(2,3-dihydro-5-benzofuranyl)pyridine-2-carboxylic acid (Compound 201): $^1$H NMR (DMSO-$d_6$): δ 7.80 (s, 1H), 7.70 (d, 1H), 6.85 (d, 3H), 6.60 (br.s, 2H), 4.60 (t, 2H), 3.30 (t, 3H).
4-Amino-3,5-difluoro-6-(6-chlorophenyl)pyridine-2-carboxylic acid (Compound 202): mp 166–67° C. dec.
4-Amino-3,5-difluoro-6-(4-methylphenyl)pyridine-2-carboxylic acid (Compound 203): mp 144–145° C.
4-Amino-3,5-difluoro-6-(2-chloro-4-methylphenyl)pyridine-2-carboxylic acid (Compound 204): $^1$H NMR (DMSO-$d_6$): δ 7.42 (s, 1H), 7.30 (m, 2H), 6.80 (br.s, 2H), 2.40 (s, 3H).
4-Amino-3,5-difluoro-6-(2,4-dichlorophenyl)pyridine-2-carboxylic acid (Compound 205): $^1$H NMR (CD$_3$OD): δ 7.4 (m, 2H), 7.58 (m, 1H).
4-Amino-3,5-difluoro-6-(4-chloro-2-fluorophenyl)pyridine-2-carboxylic acid (Compound 206): mp 155–56° C.
4-Amino-3,5-difluoro-6-(3,4-methylenedioxyphenyl)pyridine-2-carboxylic acid (Compound 207): mp 174–75° C.
4-Amino-3,5-dichloro-6-(2-thienyl)pyridine-2-carboxylic acid (Compound 208): mp 144° C.
4-Amino-3-chloro-6-(4-pyridinyl)pyridine-2-carboxylic acid (Compound 209): mp 155° C. dec.
4-Amino-3,5-dichloro-6-(2-furfuryl)pyridine-2-carboxylic acid (Compound 210): mp 152° C.
4-Amino-3-chloro-6-(2-thienyl)pyridine-2-carboxylic acid (Compound 211): $^1$H NMR (DMSO-$d_6$): δ 7.46 (m, 2H), 7.07 (m, 1H), 6.93 (s, 1H), 6.09 (m, 2H)
4-Amino-3-chloro-6-(2-furfuryl)pyridine-2-carboxylic acid (Compound 212): $^1$H NMR (DMSO-$d_6$): δ 7.71 (m, 1H), 6.89 (s, 1H), 6.82 (m, 1H), 5.56 (m, 1H), 6.17 (m, 2H).
4-Amino-3-chloro-6-(6-methoxy-3-pyridinyl)pyridine-2-carboxylic acid (Compound 213): mp 110° C. dec.
4-Amino-3-chloro-6-(2-pyridinyl)pyridine-2-carboxylic acid (Compound 214): mp 185° C. dec.
4-Amino-3-chloro-6-(5-chloro-2-thienyl)pyridine-2-carboxylic acid (Compound 215): mp 178–179° C.
4-Amino-3-chloro-6-(3-thienyl)pyridine-2-carboxylic acid (Compound 216): mp 184° C.
4-Amino-3-chloro-6-(2,3-dihydro-5-benzofuranyl)pyridine-2-carboxylic acid (Compound 217): mp 218–20° C.
4-Amino-3-chloro-6-(5-methyl-2-thienyl)pyridine-2-carboxylic acid (Compound 218): mp 175–6° C.
4-Amino-6-(2-benzofuranyl)-3-chloropyridine-2-carboxylic acid (Compound 219): mp 151° C.
4-Amino-3-chloro-6-(2-pyrazinyl)pyridine-2-carboxylic acid (Compound 220): mp 172–73° C.
4-Amino-3-chloro-5-fluoro-6-(6-chloro-3-pyridinyl)pyridine-2-carboxylic acid (Compound 221): mp 125° C. dec.
4-Amino-3-chloro-6-(2-thiazolyl)pyridine-2-carboxylic acid (Compound 222): mp 184–85° C.
4-Amino-3-chloro-6-(1-methyl-1H-pyrazol-5-yl)pyridine-2-carboxylic acid (Compound 223): mp 230–32° C.
4-Amino-3-chloro-6-(2-benzothienyl)pyridine-2-carboxylic acid (Compound 224): mp 176° C.
4-Amino-3-chloro-6-(6-chloro-3-pyridinyl)pyridine-2-carboxylic acid (Compound 225): mp 110–114° C.
4-Amino-3-chloro-6-(2-benzoxazolyl)pyridine-2-carboxylic acid (Compound 226): mp 262° C. dec.
4-Amino-3-chloro-6-(2-(5-methyl-1,3,4-oxadiazolyl))pyridine-2-carboxylic acid (Compound 227): mp 210° C.

4-Amino-3-chloro-6-(5-pyrimidinyl)pyridine-2-carboxylic acid (Compound 228): mp 180° C.

4-Amino-3-chloro-6-(2-(5-methyl-1,3,4-thiadiazolyl))pyridine-2-carboxylic acid (Compound 229): mp 200–201° C.

4-Amino-3-chloro-6-(2-benzothiazolyl)pyridine-2-carboxylic acid (Compound 230): mp 283° C.

4-Amino-3-chloro-6-(5-oxazolyl)pyridine-2-carboxylic acid (Compound 231): mp 166–170° C.

4-Amino-3-chloro-6-(2-benzoxazolyl)pyridine-2-carboxylic acid (Compound 232): mp 262° C. (dec).

4-Amino-3-chloro-6-(3-(6-methyl)pyridazinyl)pyridine-2-carboxylic acid (Compound 233): mp 212–13° C.

4-Amino-3-chloro-6-(3-(6-methyl)pyridazyl)pyridine-2-carboxylic acid (Compound 234): mp 212–213° C.

4-Amino-3-chloro-6-(4-(2-methylthiazolyl))pyridine-2-carboxylic acid (Compound 235): $^1$H NMR (DMSO-d$_6$): δ 8.01 (s,1H), 7.53 (s,1H), 6.76 (br.s, 2H), 2.71 (s, 3H).

4-Amino-3,5-dichloro-6-(4-(2-methylthiazolyl))pyridine-2-carboxylic acid (Compound 236): $^1$H NMR (DMSO-d$_6$): δ 7.88 (s,1H), 6.98 (br.s, 2H), 2.71 (s, 3H).

4-Amino-3,5-dichloro-6-(5-chloro-2-furanyl)pyridine-2-carboxylic acid (Compound 237): $^1$H NMR (DMSO-d$_6$): δ 7.33 (d, J=3.6 Hz, 1H), 7.05 (br.s, 2H), 6.72(d,J=3.6 Hz, 1H).

4-Amino-3-chloro-5-fluoro-6-(4-(2-methylthiazolyl))pyridine-2-carboxylic acid (Compound 238): $^1$H NMR (DMSO-d$_6$): δ 7.73 (s,1H), 6.90 (br.s, 2H), 2.43 (s, 3H).

4-Amino-3-chloro-6-(2-methoxy-5-pyrimidinyl)pyridine-2-carboxylic acid (Compound 239): mp 153° C.

4-Amino-3-chloro-6-(2-(5-methylthiazolyl))pyridine-2-carboxylic acid (Compound 240): mp 166–167° C.

4-Amino-3,5-dichloro-6-(5-thiazolyl)pyridine-2-carboxylic acid (Compound 241): mp 175–177° C.

38. Preparation of Methyl 4-amino-3-chloro-6-(4-hydroxymethylphenyl)pyridine-2-carboxylate (Compound 242)

Sodium borohydride (112 mg, 3 mmol) was slowly added to a solution of methyl 4-amino-3-chloro-6-(4-formylphenyl)pyridine-2-carboxylate (2.87 g, 9.87 mmol) in methanol/dichloromethane (1:1, 100 mL) cooled by an ice bath. After the addition was complete, the ice bath was removed and the reaction mixture was stirred for 15 minutes and then concentrated. The residue was dissolved in ethyl acetate/water and the organic phase was washed with brine, dried (MgSO$_4$) and concentrated. The residue was purified by column chromatography over silica gel (40% ethyl acetate/hexane) to yield methyl 4-amino-3-chloro-6-(4-hydroxymethylphenyl)pyridine-2-carboxylate (2.5 g 8.54 mmol), mp 138–139° C.

39. Preparation of Methyl 4-amino-3-chloro-6-[4-(fluoromethyl)phenyl] Pyridine-2-carboxylate (Compound 243)

(Diethylamino)sulfur trifluoride (0.73 mL, 5.5 mmol) was added dropwise to a solution of methyl 4-amino-3-chloro-6-(4-hydroxymethylphenyl)pyridine-2-carboxylate (1.46 g, 5.0 mmol) in dichloromethane (35 mL) at 0° C. The reaction mixture was stirred for 15 minutes and then quenched with ice followed by water. The product was extracted with ethyl acetate and the organic phase was washed with brine and concentrated. The residue was purified by column chromatography (dichloromethane/hexane) giving methyl 4-amino-3-chloro-6-(4-fluoromethylphenyl)pyridine-2-carboxylate (480 mg, 1.6 mmol), mp 95–97° C.

40. Preparation of Decyl 4-amino-3-chloro-5-fluoro-6-(4-chlorophenyl)pyridine-2-carboxylate (Compound 244)

Methyl 4-amino-3-chloro-5-fluoro-6-(4-chlorophenyl)pyridine-2-carboxylate (0.545 g, 1.73 mmol) was suspended in decanol (20 mL) and titanium methoxide (0.029 g, 1.73 mmol) was added and the mixture heated under reflux for five hours. The reaction mixture was concentrated and the residue dissolved in ethyl acetate (100 mL) and washed with water (100 mL) and saturated sodium bicarbonate solution (100 mL). The organic phase was dried (MgSO$_4$) and concentrated to give decyl 4-amino-3-chloro-5-fluoro-6-(4-chlorophenyl)pyridine-2-carboxylate (0.67 g, 1.5 mmol), mp 62–63° C.

The following esters were prepared in an analogous manner:

2-Butoxyethyl 4-amino-3-chloro-5-fluoro-6-(4-chlorophenyl)pyridine-2-carboxylate (Compound 245) mp 103–104° C.

2-Ethylhexyl 4-amino-3-chloro-5-fluoro-6-(4-chlorophenyl)pyridine-2-carboxylate (Compound 246): $^1$H NMR (CDCl$_3$): δ 7.89 (d, 2H), 7.41 (d, 2H), 4.32 (d,2H), 1.94 (m, 6H), 1.75 (m, 1H), 1.40 (m, 8H).

2-Methylheptyl 4-amino-3-chloro-5-fluoro-6-(4-chlorophenyl)pyridine-2-carboxylate (Compound 247): $^1$H NMR (CDCl$_3$): δ 7.91 (d, 2H), 7.44 (d, 2H), 5.23 (m, 1H), 4.85 (s, 2H), 1.89 (t, 3H), 1.70 (m, 1H), 1.38 (d, 2H), 1.26 (m, 8H).

2-Butoxyethyl 4-amino-3-chloro-6-(4-methylphenyl)pyridine-2-carboxylate (Compound 248): $^1$H NMR (CDCl$_3$): δ 7.75 (d, 2H), 7.19 (d, 2H), 7.04 (s, 1H), 4.83 (s, 2H), 4.55 (t, 2H), 3.78 (t, 2H), 3.53 (t, 2H), 2.37 (s, 3H), 1.91 (t, 3H), 1.58 (m, 2H), 1.38 (m, 2H).

Butyl 4-amino-3-chloro-6-(4-methylphenyl)pyridine-2-carboxylate (Compound 249): mp 60–62° C.

Ethoxybutyl 4-amino-3-chloro-6-(4-methylphenyl)pyridine-2-carboxylate (Compound 250): $^1$H NMR (CDCl$_3$): δ 7.81 (d, 2H), 7.22 (d, 2H), 7.08 (s, 1H), 4.79 (s, 2H), 4.53 (t, 2H), 3.63 (t, 2H), 3.52 (q, 2H), 2.41 (s, 3H), 2.10 (m, 2H), 1.22 (t, 3H).

2-Ethylbutyl 4-amino-3-chloro-6-(4-methylphenyl)pyridine-2-carboxylate (Compound 251): $^1$H NMR (CDCl$_3$): δ 7.82 (d, 2H), 7.22 (d, 2H), 4.75 (s, 2H), 4.75 (s, 2H), 2.39 (s, 2H), 2.39 (s, 2H), 1.91 (m, 6H), 1.42 (m, 8H).

Ethyl 4-amino-3-chloro-5-fluoro-6-(4-chlorophenyl)pyridine-2-carboxylate (Compound 252): mp 88–89° C.

Butoxyethyl 4-amino-3-chloro-5-fluoro-6-(4-chlorophenyl)pyridine-2-carboxylate, (Compound 253): mp 103–104° C.

2-Ethylhexyl 4-amino-3-chloro-5-fluoro-6-(4-chlorophenyl)pyridine-2-carboxylate (Compound 254): $^1$H NMR (CDCl$_3$): δ 7.91 (d, 2H), 7.41 (d, 2H), 4.86 (s, 2H), 4.32 (d, 2H), 1.94 (m, 6H), 1.75 (m, 1H), 1.40 (m, 8H).

Ethyl 4-amino-3-chloro-6-(2,4-dichlorophenyl)pyridine-2-carboxylate (Compound 255): $^1$H NMR (DMSO-d$_6$): δ 7.75 (d, 1H), 7.50 (m, 2H), 7.05 (s, 1H), 4.50 (q, 2H), 5.0 (br.s, 2H), 1.30 (t, 3H).

Propyl 4-amino-3-chloro-6-(2,4-dichlorophenyl)pyridine-2-carboxylate (Compound 256): $^1$H NMR (CDCl$_3$): δ 7.60 (d, 1H), 7.50 (m, 1H), 7.35 (m,1H), 7.05 (s,1H), 5.00 (br.s, 2H), 4.40 (t, 2H), 1.95 (m, 2H), 1.05 (t, 3H).

Butyl 4-amino-3-chloro-6-(2,4-dichlorophenyl)pyridine-2-carboxylate (Compound 257): $^1$H NMR (CDCl$_3$): δ 7.60 (d, 1H), 7.50 (m, 1H), 7.35 (m,1H), 7.05 (s, 1H), 5.00 (br.s, 2H), 4.50 (t, 2H), 1.90 (m, 2H), 1.50 (m, 2H), 1.00 (t, 3H).

Pentyl 4-amino-3-chloro-6-(2,4-dichlorophenyl)pyridine-2-carboxylate (Compound 258): $^1$H NMR (CDCl$_3$): δ 7.60 (d, 1H), 7.50 (m, 1H), 7.35 (m, 1H), 7.05 (s, 1H), 5.00 (br.s, 2H), 4.5 (t, 2H), 1.95 (m, 2H), 1.4 (m, 4H), 0.90 (t, 3H).

2-Ethylhexyl 4-amino-3-chloro-6-(2,4-dichlorophenyl) pyridine-2-carboxylate (Compound 259): $^1$H NMR (CDCl$_3$): δ 7.60 (d, 1H), 7.50 (m, 1H), 7.35 (m, 1H), 7.30 (s, 1H), 5.50 (br.s, 2H), 4.35 (d, 2H), 1.90 (m, 1H), 1.50 (m, 8H), 0.90 (m, 6H).

Decyl 4-amino-3-chloro-6-(2,4-dichlorophenyl)pyridine-2-carboxylate (Compound 260): $^1$H NMR (CDCl$_3$): δ 7.60 (d, 1H), 7.45 (br.s, 1H), 7.35 (d, 1H), 7.25(s, 1H), 4.90 (br.s, 2H), 4.40 (t, 2H), 1.80 (m, 2H), 1.30 (m, 17H).

2-Methylethyl 4-amino-3-chloro-6-(2,4-dichlorophenyl) pyridine-2-carboxylate (Compound 261): $^1$H NMR (DMSO-d$_6$): δ 7.75 (d, 1H), 7.50 (m, 2H), 7.05 (s, 1H), 5.20 (m, 1H), 3.80 (br.s, 2H), 1.40 (d, 6H).

Hexyl 4-amino-3-chloro-6-(2,4-dichlorophenyl)pyridine-2-carboxylate (Compound 262): $^1$H NMR (CDCl$_3$): δ 7.69 (d, 1H), 7.50 (m,1H), 7.30 (d, 1H), 7.05 (s, 1H), 4.95 (br.s, 2H), 4.50 (t, 2H), 1.80 (m, 2H), 1.80 (m, 4H), 1.00 (t, 2H).

Ethyl 4-amino-3-chloro-6-(4-methylphenyl)pyridine-2-carboxylate (Compound 263): mp. 129–30° C.

41. Preparation of 4-Amino-3-chloro-5-fluoro-6-(4-chlorophenyl)-2-(N-benzyl)picolinamide (Compound 264)

1-(3-Dimethylaminopropyl)-3-ethylcarbodiimide hydrochloride (80 mg, 0.415 mmol) was added to a mixture of 4-amino-3-chloro-5-fluoro-6-(4-chlorophenyl)pyridine-2-carboxylic acid (100 mg, 0.332 mmol), benzyl amine (43 mg, 0.398 mmol), N-methylmorpholine (74 mg, 0.731 mmol), 1-hydroxy-benzotriazole (91.5 mg, 0.598 mmol) in tetrahydrofuran (8 mL) at room temperature. After stirring for 16 hours, the reaction mixture was concentrated and the residue partioned between ethyl acetate and 1N hydrochloric acid. The organic layer was washed with saturated aqueous sodium bicarbonate, brine and dried (MgSO$_4$). Purification by column chromatography gave 4-amino-3-chloro-5-fluoro-6-(4-chlorophenyl)-2-(N-benzyl)picolinamide (112 mg, 0.287 mmol). $^1$H NMR (CDCl$_3$): δ 8.13 (m, 1H), 7.83 (m, 2H), 7.48–7.29 (m, 6H), 5.03 (br.s, 2H), 4.67 (d, J=6.0 Hz, 2H).

42. Preparation of Methyl 4-N-methylamino-3-chloro-5-fluoro-6-(4-chlorophenyl)pyridine-2-carboxylate (Compound 265)

A solution of methyl 4-amino-3-chloro-5-fluoro-6-(4-chlorophenyl)pyridine-2-carboxylate (1.0 g, 3.2 mmol), iodomethane (0.3 mL, 4.8 mmol), and sodium hydride (0.16 g, 3.9 mmol) in tetrahydrofuran (12 mL) was refluxed for four hours under a nitrogen atmosphere. After cooling, the solvent was evaporated off and the residue taken up into ethyl acetate (50 mL). The organic layer was washed with sodium bicarbonate (3×50 mL), dried (Na$_2$SO$_4$) and was concentrated. The product was purified by column chromatography (dichloromethane) to give methyl 4-N-methylamino-3-chloro-5-fluoro-6-(4-chlorophenyl) pyridine-2-carboxylate (0.154 g, 0.47 mmol): $^1$H NMR (CDCl$_3$): δ7.83 (d, 2H) 7.44 (d, 2H) 4.88 (s, 1H) 3.97 (s, 1H) 3.29 (d, 3H).

43. Preparation of Methyl 4-acetamido-3-chloro-6-(1-ethoxyvinyl)pyridine-2-carboxylate A solution of methyl 4-acetamido-3,6-dichloropyridine-2-carboxylate (0.988 g, 4.0 mmol), ethoxyvinyltributyltin (2.70 mL, 8.0 mmol) and cesium fluoride (1.34 g, 8.8 mmol) in dioxane (20 mL) was sparged with nitrogen for 15 minutes. Dichlorobis(triphenylphosphine)palladium(II) (0.140 g, 0.2 mmol) was then added and the mixture was heated at 100° C. for 5 hours. After cooling, ether was added and the reaction mixture filtered through a silica plug. The solvents were removed and the crude product was purified by chromatography (ethyl acetate:hexane (1:2)) to give methyl 4-acetamido-3-chloro-6-(1-ethoxyvinyl)pryidine-2-carboxylate (0.780 g, 2.6 mmol). $^1$H NMR (CDCl$_3$): δ 8.85 (s, 1H), 7.90 (br.s, 1H), 5.47 (d, J=2.0 Hz, 1H), 4.44 (d, J=2.0 Hz, 1H), 4.01 (s, 3H), 3.98 (q, J=7.0 Hz, 2H), 2.32 (s, 3H), 1.46 (t, J=7.0 Hz, 3H).

44. Preparation of Methyl 4-acetamido-3-chloro-6-(bromoacetyl)pyridine-2-carboxylate N-Bromosuccinimide (0.377 g, 2.13 mmol) was added all at once to a solution of methyl 4-acetamido-3-chloro-6-(1-ethoxyvinyl)pyridine-2-carboxylate (0.636 g, 2.13 mmol) in THF (40 mL) and water (2 mL) at room temperature. After 15 minutes, the reaction mixture was concentrated and the residue partitioned between dichloromethane and water. The organic layer was separated, dried (MgSO$_4$), and concentrated to provide methyl 4-acetamido-3-chloro-6-(bromoacetyl)pyridine-2-carboxylate (0.714 g, 2.04 mmol). $^1$H NMR (CDCl$_3$): δ 9.12 (s, 1H), 7.99 (br.s, 1H), 4.82 (s, 2H), 4.06 (s, 3H), 2.36 (s, 3H).

45. Preparation of Methyl 4-acetamido-3-chloro-6-(4-(2-methylthiazolyl))-pyridine-2-carboxylate (Compound 266)

Methyl 4-acetamido-3-chloro-6-(bromoacetyl)pyridine-2-carboxylate (0.10 g, 0.286 mmol) and thioacetamide (21.5 mg, 0.286 mmol) were combined in methanol (5 mL) and the temperature was brought to 60° C. for 15 minutes. After cooling, the reaction mixture was concentrated and the residue purified by column chromatography (ethyl actetate:hexane, 2:1) to give methyl 4-acetamido-3-chloro-6-(4-(2-methylthiazolyl))pyridine-2-carboxylate (25 mg, 0.078 mmol): $^1$H NMR (CDCl$_3$): δ 9.24 (s, 1H), 7.96 (s, 1H), 7.95 (s, 1H), 4.03 (s, 3H), 2.79 (s, 3H), 2.34 (s, 3H).

The following compounds were prepared in an analogous manner

Methyl 4-amino-3,5-dichloro-6-(4-(2-methylthiazolyl)) pyridine-2-carboxylate (Compound 267): $^1$H NMR (CDCl$_3$): δ 7.14 (s, 1H), 5.40 (br.s, 2H), 3.98 (s, 3H), 2.81 (s, 3H).

Methyl 4-amino-3-chloro-5-fluoro-6-(4-(2-methylthiazolyl))pyridine-2-carboxylate (Compound 268): $^1$H NMR (CDCl$_3$): δ 7.81 (s, 1H), 4.96 (br.s, 2H), 3.97 (s, 3H), 2.80 (s, 3H).

Methyl 4-amino-3-chloro-6-(4-(2,2,2-trifluromethylthiazolyl))pyridine-2-carboxylate (Compound 269): $^1$H NMR (CDCl$_3$): δ 8.35 (s, 1H), 7.65 (s, 1H), 4.92 (br.s, 2H), 4.04 (s, 3H), (use of triflurothioacetamide).

Methyl 4-amino-3-chloro-5-fluoro-6-(4-(2,2,2-triflurometh yl thiazolyl))pyridine-2-carboxylate (Compound 270): $^1$H NMR (CDCl$_3$): δ 8.28 (s, 1H), 5.03 (br.s, 2H), 4.02 (s, 3H), (use of triflurothioacetamide).

46. Preparation of Methyl 3,4,5-trichloro-6-(5-chloro-2-furyl)pyridine-2-carboxylate Benyltrimethylammonium tetrachloroiodate (292 mg, 0.70 mmol) was added to a solution of methyl-3,4,5-trichloro-6-(2-furyl)pyridine-2-carboxylate (101 mg, 0.33 mmol) in acetic acid (5 mL). After one hour, the suspension was diluted with diethyl ether and the organic mixture was washed with 0.1 N sodium thiosulphate, 0.1 N sodium bicarbonate and dried (MgSO$_4$). The residue was purified by column chromatography (diethyl ether:hexane, 5:95) to give methyl 3,4,5-trichloro-6-(5-chloro-2-furyl)pyridine-2-carboxylate (58 mg, 0.17 mmol): $^1$H NMR (CDCl$_3$): δ 7.41 (d, J=3.6 Hz, 1H), 6.40 (d, J=3.6 Hz, 1H), 4.05 (s, 3H).

47. Preparation of Methyl 6-(5-bromo-2-thiazolyl)-3,4-dichloropyridine-2-carboxylate and Methyl 4-bromo-6-(5-bromo-2-thiazolyl)-3-chloropyridine-2-carboxylate Bromine (0.188 mL, 3.67 mmol) was aded to a solution of methyl 3,4-dichloro-6-(2-thiazolyl)pyridine-2-carboxylate (1.01 g, 3.5 mmol) in acetic acid (15 mL). The mixture was heated at 75° C. overnight. After cooling, saturated sodium bicarbonate was added and the mixture extracted with diethyl ether. The organic layer was washed with saturated metabisulfite, brine and dried (MgSO$_4$). The residue was purified by column chromatography (ethyl acetate:hexane, 1:4) to give an unseparated mixture of methyl 6-(5-bromo-2-thiazolyl)-3,4-dichloropyridine-2-carboxylate and methyl 4-bromo-6-(5-bromo-2-thiazolyl)-3-chloropyridine-2-carboxylate (0.277 mg): $^1$H NMR (CDCl$_3$): δ 8.51 (s, 0.33H), 8.34 (s, 0.66H), 7.84 (s, 1H), 4.07 (s, 3H) and unreacted of methyl 3,4-dichloro-6-(2-thiazolyl)pyridine-2-carboxylate (185 mg).

48. Preparation of Herbicidal Compositions

In the following illustrative compositions, parts and percentages are by weight.

Emulsifiable Concentrates

| | WT % |
|---|---|
| Formulation A | |
| Compound 18 | 26.2 |
| Polyglycol 26-3 | 5.2 |
| Nonionic emulsifier-(di-sec-butyl)-phenyl-poly(oxypropylene)block polymer with (oxyethylene). The polyoxyethelene content is about 12 moles. | |
| Witconate P12-20 (Anionic emulsifier-calcium dodecylbenzene sulfonate-60 wt. % active) | 5.2 |
| Aromatic 100 (Xylene range aromatic solvent) | 63.4 |
| Formulation B | |
| Compound 22 | 3.5 |
| Sunspray 11 N (paraffin oil) | 40.0 |
| Polyglycol 26-3 | 19.0 |
| Oleic acid | 1.0 |
| Xylene range aromatic solvent | 36.5 |
| Formulation C | |
| Compound 22 | 13.2 |
| Stepon C-65 | 25.7 |
| Ethomeen T/25 | 7.7 |
| Ethomeen T/15 | 18.0 |
| Xylene range aromatic solvent | 35.4 |
| Formulation D | |
| Compound 128 | 30.0 |
| Agrimer Al-10LC (emulsifier) | 3.0 |
| N-methyl-2-pyrrolidone | 67.0 |
| Formulation E | |
| Compound 128 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

| | WT % |
|---|---|
| Formulation F | |
| Compound 65 | 26.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

| | WT % |
|---|---|
| Formulation G | |
| Compound 39 | 62.4 |
| Polyfon H (sodium salt of lignin sulfonate) | 6.0 |
| Sellogen HR (sodium naphthalene sulfonate) | 4.0 |
| Zeosyl 100 | 27.6 |
| Formulation H | |
| Compound 128 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

| | WT % |
|---|---|
| Formulation I | |
| Compound 165 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

| | WT % |
|---|---|
| Formulation J | |
| Compound 65 | 5.0 |
| Celetom MP-88 | 95.0 |

The active ingredient is applied in a polar solvent such as N-methyl-pyrrollidinone, cyclohexanone, gamma-butyrolactone, etc. to the Celetom MP 88 carrier or to other suitable carriers. The resulting granules can be applied by hand, granule applicator, airplane, etc. in order to control weeds.

| | WT % |
|---|---|
| Formulation K | |
| Compound 225 | 1.0 |
| Polyfon H | 8.0 |

-continued

Formulation K

|  | WT % |
|---|---|
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

Formulation L

|  | Wt % |
|---|---|
| Compound 165 | 3.67 |
| Monoethanolamine pH buffer | 0.5 |
| Water | 95.83 |

The active ingredient is dissolved in and appropriate amount of water and the additional monoethanolamine is added as a buffer. A water-soluble surfactant may be added. Other aids may be incorporated to improve physical, chemical and/or formulation properties.

49. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximate 15 hr photoperiod which was maintained at about 23–29° C. during the day and 22–28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with an aqueous mixture containing acetone, water, isopropyl alcohol, DMSO, At plus 411 F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "Probit Analysis" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Tables 1–2. Selectivity to wheat and corn is shown in Tables 3 and 4.

TABLE 1

Post-emergent % control

| Compound | Rate (ppm) | XANST | CHEAL | ECHCG | CYPES |
|---|---|---|---|---|---|
| 12 | 500 | 100 | 95 | 95 | 30 |
| 13 | 250 | 100 | 100 | 70 | 80 |
| 17 | 250 | 100 | 100 | 70 | 70 |
| 19 | 250 | 100 | 95 | 80 | 90 |
| 20 | 250 | 100 | 100 | 70 | 50 |
| 21 | 250 | 100 | 100 | 0 | 70 |
| 27 | 250 | 95 | 95 | 70 | 60 |
| 28 | 250 | 100 | 100 | 75 | 80 |
| 29 | 500 | 100 | 100 | 95 | 80 |
| 33 | 500 | 100 | 100 | 30 | 10 |
| 175 | 500 | 100 | 99 | 80 | 0 |
| 149 | 500 | 100 | 100 | 95 | 100 |
| 39 | 500 | 100 | 100 | 95 | 99 |
| 43 | 500 | 100 | 100 | 95 | 100 |
| 44 | 250 | 100 | 80 | 30 | 70 |
| 47 | 500 | 90 | 90 | 80 | 0 |
| 49 | 125 | 100 | 80 | 10 | 30 |
| 52 | 500 | 100 | 100 | 90 | 40 |
| 59 | 500 | 100 | 100 | 80 | 50 |
| 58 | 500 | 100 | 100 | 70 | 70 |
| 59 | 500 | 100 | 100 | 90 | 100 |
| 84 | 250 | 100 | 100 | 98 | 100 |
| 85 | 250 | 100 | 100 | 99 | 70 |
| 86 | 500 | 100 | 100 | 90 | 90 |
| 88 | 250 | 100 | 100 | 85 | 95 |
| 89 | 250 | 100 | 100 | 90 | 50 |
| 90 | 500 | 100 | 100 | 98 | 90 |
| 91 | 500 | 100 | 100 | 90 | 80 |
| 93 | 500 | 100 | 95 | 90 | 80 |
| 94 | 500 | 100 | 100 | 90 | 90 |
| 95 | 125 | 80 | 90 | 70 | 60 |
| 98 | 125 | 90 | 90 | 50 | 70 |
| 111 | 250 | 100 | 100 | 70 | 80 |
| 132 | 500 | 100 | 90 | 80 | 0 |
| 136 | 250 | 100 | 100 | 70 | 80 |
| 138 | 250 | 100 | 100 | 50 | 20 |
| 139 | 250 | 100 | 95 | 70 | 30 |
| 141 | 250 | 100 | 100 | 80 | 10 |
| 143 | 500 | 100 | 100 | 70 | 40 |
| 146 | 250 | 100 | 100 | 85 | 98 |
| 149 | 500 | 100 | 100 | 95 | 90 |
| 150 | 500 | 100 | 100 | 95 | 95 |
| 151 | 500 | 100 | 100 | 100 | 85 |
| 152 | 125 | 100 | 100 | 90 | 95 |
| 153 | 500 | 100 | 98 | 95 | 70 |
| 154 | 500 | 100 | 100 | 100 | 100 |
| 158 | 500 | 100 | 100 | 95 | 70 |
| 163 | 250 | 100 | 95 | 70 | 70 |
| 168 | 500 | 100 | 100 | 85 | 90 |
| 170 | 500 | 100 | 100 | 80 | 70 |
| 171 | 500 | 100 | 95 | 80 | 60 |
| 172 | 125 | 100 | 90 | 90 | 90 |
| 173 | 500 | 100 | 100 | 100 | 100 |

TABLE 1-continued

Post-emergent % control

| Compound | Rate (ppm) | XANST | CHEAL | ECHCG | CYPES |
|---|---|---|---|---|---|
| 180 | 250 | 80 | 100 | 70 | 30 |
| 181 | 500 | 100 | 100 | 100 | 100 |
| 184 | 125 | 100 | 70 | 70 | 40 |
| 196 | 250 | 100 | 100 | 100 | 98 |
| 197 | 250 | 100 | 100 | 90 | 95 |
| 198 | 500 | 100 | 100 | 90 | 90 |
| 199 | 250 | 100 | 100 | 85 | 95 |
| 200 | 500 | 100 | 95 | 95 | 90 |
| 202 | 500 | 100 | 100 | 100 | 95 |
| 203 | 500 | 100 | 100 | 95 | 95 |
| 206 | 500 | 99 | 95 | 85 | 70 |
| 207 | 125 | 90 | 70 | 70 | 40 |
| 215 | 125 | 100 | 100 | 70 | 70 |
| 219 | 250 | 100 | 100 | 80 | 0 |
| 224 | 125 | 100 | 100 | 85 | 30 |
| 225 | 125 | 90 | 70 | 40 | 60 |

XANST = Cocklebur (*Xanthium strumarium*)
CHEAL = Lambsquarter (*Chenopodium album*)
ECHCG = Barnyardgrass (*Echinochloa crus-galli*)
CYPES = Yellow nutsedge (*Cyperus esculentus*)

TABLE 2

Post-emergent % control

| Compound | Rate (ppm) | XANST | CHEAL | ECHCG | CYPES |
|---|---|---|---|---|---|
| 183 | 125 | 100 | 100 | 100 | 100 |
| 84 | 125 | 100 | 100 | 98 | 90 |
| 86 | 125 | 100 | 100 | 80 | 100 |
| 88 | 125 | 100 | 100 | 85 | 95 |
| 121 | 125 | 100 | 90 | 80 | 80 |
| 136 | 125 | 100 | 100 | 70 | 70 |
| 146 | 125 | 100 | 100 | 75 | 95 |
| 151 | 125 | 100 | 100 | 85 | 90 |
| 154 | 125 | 100 | 100 | 70 | 90 |
| 163 | 125 | 100 | 90 | 70 | 70 |
| 181 | 125 | 100 | 100 | 70 | 85 |
| 189 | 125 | 90 | 90 | 90 | 90 |
| 196 | 125 | 100 | 100 | 100 | 100 |
| 197 | 125 | 100 | 100 | 85 | 85 |
| 198 | 125 | 100 | 100 | 70 | 98 |
| 199 | 125 | 100 | 100 | 80 | 90 |
| 200 | 125 | 90 | 80 | 70 | 90 |
| 202 | 125 | 100 | 100 | 70 | 80 |

XANST = Cocklebur ((*Xanthium strumarium*)
CHEAL = Lambsquarter (*Chenopodium album*)
ECHCG = Barnyardgrass (*Echinochloa crus-galli*)
CYPES = Yellow nutsedge (*Cyperus esculentus*)

TABLE 3

Post-emergent % control

| Compound | Rate | CHEAL | AMARE | TRZAS |
|---|---|---|---|---|
| 53 | 62.5 | 80 | 70 | 0 |
| 52 | 62.5 | 100 | 70 | 10 |
| 132 | 62.5 | 100 | 70 | 0 |
| 12 | 62.5 | 100 | 70 | 0 |
| 43 | 62.5 | 100 | 100 | 10 |
| 153 | 62.5 | 90 | 100 | 10 |
| 29 | 62.5 | 80 | 90 | 10 |
| 21 | 62.5 | 90 | 70 | 10 |
| 136 | 62.5 | 100 | 100 | 0 |
| 20 | 62.5 | 90 | 100 | 10 |

CHEAL = Lambsquarter (*Chenopodium album*)
AMARE = Pigweed (redroot) (*Amaranthus retroflexus*)
TRZAS = Wheat(var. Merica) (*Triticum aestivum*)

TABLE 4

Post-emergent % control

| Compound | Rate | XANST | CHEAL | AMARE | ZEAMX |
|---|---|---|---|---|---|
| 146 | 62.5 | 100 | 100 | 100 | 0 |
| 53 | 62.5 | 100 | 80 | 70 | 10 |
| 45 | 62.5 | 90 | 90 | 100 | 0 |
| 155 | 62.5 | 100 | 90 | 100 | 0 |
| 12 | 62.5 | 100 | 100 | 70 | 10 |
| 43 | 62.5 | 100 | 100 | 100 | 0 |
| 21 | 62.5 | 95 | 90 | 70 | 0 |
| 58 | 62.5 | 90 | 100 | 100 | 0 |

XANST = Cocklebur (*Xanthium strumarium*)
CHEAL = Lambsquarter (*Chenopodium album*)
AMARE = Pigweed (redroot) (*Amaranthus retroflexus*)
ZEAMX = Corn (#14 3377) (*Zea mays*)

50. Evaluation of Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 2 mL aliquots of the stock solution with 15 mL of the mixture and lower concentrations were prepared by serial dilution of the stock solution. A 2.5 mL aliquot of each solution of known concentration was sprayed evenly onto the soil surface (113 sq. cm) of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture.

The treated pots and control pots were placed in a greenhouse maintained with an approximate 15 hr photoperiod and temperatures of about 23–29° C. during the day and 22–28° C. during the night. Nutrients and water were added on a regular basis and supplemental lighting was provided with overhead metal halide 1000-Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination.

Some of the compounds tested, application rates employed, plant species tested, and results are given in Table 5.

TABLE 5

Pre-emergent % control

| Compound | Rate (ppm) | CHEAL | AMARE | DIGSA | SETFA |
|---|---|---|---|---|---|
| 12 | 560 | 98 | 100 | 40 | 30 |
| 13 | 560 | 100 | 100 | 90 | 100 |
| 17 | 560 | 100 | 100 | 100 | 100 |
| 19 | 560 | 100 | 100 | 100 | 100 |
| 20 | 560 | 100 | 100 | 100 | 100 |
| 21 | 560 | 100 | 100 | 100 | 80 |
| 27 | 560 | 100 | 100 | 100 | 100 |
| 28 | 560 | 100 | 100 | 100 | 100 |
| 29 | 560 | 100 | 95 | 100 | 90 |
| 30 | 560 | 90 | 100 | 100 | 70 |
| 39 | 140 | 95 | 100 | 95 | 75 |
| 43 | 560 | 100 | 100 | 100 | 98 |
| 52 | 140 | 100 | 100 | 100 | 95 |
| 53 | 560 | 100 | 100 | 100 | 100 |
| 59 | 280 | 100 | 100 | 100 | 100 |
| 84 | 560 | 100 | 100 | 100 | 100 |
| 86 | 560 | 100 | 100 | 40 | 40 |
| 88 | 560 | 100 | 100 | 70 | 70 |
| 89 | 560 | 100 | 100 | 90 | 85 |
| 90 | 560 | 100 | 100 | 100 | 100 |
| 91 | 560 | 90 | 100 | 100 | 60 |
| 93 | 560 | 100 | 100 | 30 | 50 |
| 132 | 140 | 100 | 90 | 100 | 95 |
| 136 | 560 | 100 | 100 | 100 | 100 |
| 138 | 560 | 100 | 100 | 100 | 98 |
| 139 | 560 | 100 | 100 | 100 | 100 |
| 141 | 560 | 100 | 98 | 60 | 70 |
| 143 | 560 | 100 | 100 | 100 | 100 |
| 146 | 560 | 100 | 100 | 80 | 90 |
| 149 | 140 | 100 | 100 | 100 | 100 |
| 150 | 140 | 100 | 100 | 90 | 100 |
| 151 | 140 | 100 | 100 | 100 | 100 |
| 152 | 140 | 100 | 95 | 100 | 100 |
| 153 | 560 | 100 | 100 | 100 | 100 |
| 154 | 140 | 100 | 100 | 100 | 100 |
| 158 | 140 | 100 | 100 | 98 | 100 |
| 163 | 140 | 100 | 98 | 100 | 95 |
| 168 | 140 | 100 | 100 | 100 | 100 |
| 172 | 140 | 100 | 95 | 95 | 90 |
| 173 | 560 | 100 | 100 | 100 | 100 |
| 175 | 140 | 100 | 95 | 100 | 95 |
| 149 | 140 | 100 | 100 | 100 | 95 |
| 179 | 560 | 100 | 100 | 98 | 98 |
| 180 | 560 | 100 | 100 | 95 | 100 |
| 181 | 140 | 100 | 100 | 100 | 100 |
| 184 | 140 | 90 | 85 | 90 | 70 |
| 189 | 140 | 100 | 100 | 100 | 100 |
| 196 | 560 | 100 | 100 | 100 | 100 |
| 197 | 560 | 100 | 100 | 100 | 100 |
| 198 | 560 | 100 | 100 | 80 | 90 |
| 202 | 140 | 95 | 100 | 100 | 95 |
| 203 | 140 | 95 | 100 | 100 | 85 |
| 207 | 140 | NT | 100 | 95 | 50 |

CHEAL = Lambsquarter (*Chenopodium album*)
AMARE = Pigweed (redroot) (*Amaranthus retroflexus*)
DIGSA = Crabgrass(large) (*Digitaria sanguinalis*)
SETFA = Giant Foxtail (*Setaria faberi*)

What is claimed is:

1. A compound of the formula I

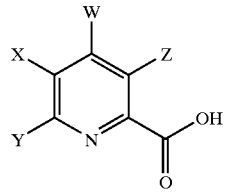

I wherein

X represents H, halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano;

Y represents an aryl group selected from the group consisting of a phenyl, indanyl or naphthyl or a heteroaryl group selected from the group of 5- or 6-membered heteroaromatic rings containing one or more heteroatoms which may be fused to other aromatic systems, the aryl or heteroaryl group being unsubstituted or substituted with one or more substituents selected from halogen, hydroxy, nitro, cyano, aryloxy, formyl, $C_1$–$C_6$ alkyl, $C_2$–$C_6$ alkenyl, $C_2$–$C_6$ alkynyl, $C_1$–$C_6$ alkoxy, halogenated $C_1$–$C_6$ alkyl, halogenated $C_1$–$C_6$ alkoxy, $C_1$–$C_6$ acyl, $C_1$–$C_6$ alkylthio, $C_1$–$C_6$ alkylsulfinyl, $C_1$–$C_6$ alkylsulfonyl, aryl, $C_1$–$C_6$ OC(O)alkyl, $C_1$–$C_6$ NHC(O)alkyl, C(O)OH, $C_1$–$C_6$ C(O)alkyl, C(O)$NH_2$, $C_1$–$C_6$ C(O)NHalkyl, $C_1$–$C_6$ C(O)N(alkyl)$_2$, —$OCH_2CH_2$—, —$OCH_2CH_2CH_2$—, —$OCH_2O$— or —$OCH_2CH_2O$—;

Z represents halogen, $C_1$–$C_6$ alkyl, $C_1$–$C_6$ alkoxy, $C_1$–$C_6$ alkylthio, aryloxy, nitro, $C_1$–$C_6$ haloalkyl, $C_1$–$C_6$ haloalkoxy, thiocyanide, or cyano; and W represents —$NO_2$, —$N_3$, —$NR_1R_2$, —N=$CR_3R_4$ or —NHN=$CR_3R_4$ wherein $R_1$ and $R_2$ independently represent H, $C_1$–$C_6$ alkyl, $C_3$–$C_6$ alkenyl, $C_3$–$C_6$ alkynyl, aryl, heteroaryl, hydroxy, $C_1$–$C_6$ alkoxy, amino, $C_1$–$C_6$ acyl, $C_1$–$C_6$ carboalkoxy, $C_1$–$C_6$ alkylcarbamyl, $C_1$–$C_6$ alkylsulfonyl, $C_1$–$C_6$ trialkylsilyl or $C_1$–$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$–$C_6$ alkyl, $C_3$–$C_6$ alkenyl, $C_3$–$C_6$ alkynyl, aryl or heteroaryl or $R_3$ and $R_4$ taken together with =C represent a 5- or 6-membered saturated ring; and agriculturally acceptable derivatives of the carboxylic acid group.

2. The compounds of claim 1 in which X represents H or F.

3. The compounds of claim 1 in which Y represents a heteroaryl group selected from the group consisting of

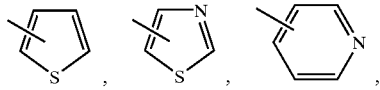

the heteroaryl group being unsubstituted or substituted with one or more halogen, $C_1$–$C_2$ alkyl or $C_1$–$C_2$ haloalkyl groups.

4. The compounds of claim 1 in which Y represents a phenyl group unsubstituted or substituted with one or more halogen, $C_1$–$C_2$ alkyl or $C_1$–$C_2$ haloalkyl groups.

5. The compounds of claim 4 in which Y represents a para-substituted phenyl group.

6. The compound of claim 1 in which Z represents Cl.

7. The compound of claim 1 in which W represents $NR_1R_2$ where $R_1$ and $R_2$ independently represent H or $C_1$–$C_6$ alkyl.

8. The compound of claim 1 in which X represents H or F, Y represents a phenyl group unsubstituted or substituted with one or more halogen, $C_1$–$C_2$ alkyl or $C_1$–$C_2$ haloalkyl groups, Z represents Cl and W represents $NR_1R_2$ where $R_1$ and $R_2$ independently represent H or $C_1$–$C_6$ alkyl.

9. A herbicidal composition comprising a herbicidally effective amount of a compound of Formula I, as claimed in any of claims 1 to 8, in admixture with an agriculturally acceptable adjuvant or carrier.

10. A method of controlling undesirable vegetation which comprises contacting the vegetation or the locus thereof with or applying to the soil to control the emergence of vegetation an herbicidally effective amount of a compound of Formula I, as claimed in any of claims 1 to 8.

* * * * *